US008354504B2

(12) United States Patent
Chappell et al.

(10) Patent No.: US 8,354,504 B2
(45) Date of Patent: Jan. 15, 2013

(54) CHIMERIC ISOPRENOID SYNTHASES AND USES THEREOF

(75) Inventors: Joseph Chappell, Lexington, KY (US);
Kyoungwhan Back, Kwangju (KR)

(73) Assignee: The Board of Trustees of The University of Kentucky, Lexington, KY (US)

( * ) Notice: Subject to any disclaimer, the term of this patent is extended or adjusted under 35 U.S.C. 154(b) by 0 days.

(21) Appl. No.: 12/927,805

(22) Filed: Nov. 23, 2010

(65) Prior Publication Data
US 2011/0081703 A1     Apr. 7, 2011

Related U.S. Application Data

(60) Continuation of application No. 11/932,489, filed on Oct. 31, 2007, now abandoned, which is a continuation of application No. 10/717,500, filed on Nov. 21, 2003, which is a continuation of application No. 09/514,513, filed on Feb. 28, 2000, now Pat. No. 7,186,891, which is a division of application No. 09/134,699, filed on Aug. 14, 1998, now Pat. No. 6,072,045, which is a continuation of application No. 08/631,341, filed on Apr. 12, 1996, now Pat. No. 5,824,774.

(51) Int. Cl.
*C07K 14/415* (2006.01)
(52) U.S. Cl. ......... 530/379; 530/350; 530/370; 435/183
(58) Field of Classification Search ........ 536/23.1–23.6; 435/182
See application file for complete search history.

(56) References Cited

U.S. PATENT DOCUMENTS

| | | | | |
|---|---|---|---|---|
| 5,589,619 A | 12/1996 | Chappell et al. | ............. | 800/205 |
| 5,744,341 A | 4/1998 | Cunningham, Jr. et al. | .. | 435/189 |
| 5,766,911 A | 6/1998 | Koike et al. | .................... | 435/193 |
| 5,824,774 A * | 10/1998 | Chappell et al. | ............. | 530/350 |
| 5,871,988 A | 2/1999 | Croteau et al. | ................ | 435/183 |
| 5,981,843 A | 11/1999 | Chappell et al. | ............. | 800/301 |
| 6,072,045 A | 6/2000 | Chappell et al. | ............. | 536/23.1 |
| 6,100,451 A | 8/2000 | Chappell et al. | ............. | 800/298 |
| 6,468,772 B1 | 10/2002 | Chappell et al. | ............. | 435/183 |
| 6,495,354 B2 | 12/2002 | Chappell et al. | ............. | 435/183 |
| 6,559,297 B2 | 5/2003 | Chappell et al. | ............. | 536/23.1 |
| 6,569,656 B2 | 5/2003 | Chappell et al. | ............. | 435/183 |
| 6,645,762 B2 | 11/2003 | Chappell et al. | ............. | 435/325 |
| 6,890,752 B2 | 5/2005 | Chappell et al. | ............. | 435/325 |
| 7,186,891 B1 | 3/2007 | Chappell et al. | ............. | 800/298 |
| 7,405,057 B2 | 7/2008 | Chappell et al. | ............. | 435/69.1 |
| 7,442,785 B2 | 10/2008 | Chappell et al. | ............. | 536/23.6 |
| 8,106,260 B2 * | 1/2012 | Chappell et al. | ............. | 800/298 |
| 8,192,950 B2 | 6/2012 | Chappell et al. | ................ | 435/41 |
| 2003/0166255 A1 | 9/2003 | Chappell | .................... | 435/252.3 |
| 2004/0078840 A1 | 4/2004 | Chappell et al. | ............. | 800/278 |
| 2006/0218661 A1 | 9/2006 | Chappell et al. | ............. | 800/278 |
| 2007/0089198 A1 | 4/2007 | Chappell et al. | ............. | 800/280 |
| 2007/0231861 A1 | 10/2007 | Millis et al. | .................. | 435/69.1 |
| 2007/0238157 A1 | 10/2007 | Millis et al. | .................... | 435/166 |
| 2007/0238159 A1 | 10/2007 | Millis et al. | ............. | 435/252.33 |
| 2007/0238160 A1 | 10/2007 | Millis et al. | ............. | 435/252.33 |
| 2008/0171378 A1 | 7/2008 | Keasling | ................... | 435/254.21 |
| 2008/0178354 A1 | 7/2008 | Chappell et al. | ............. | 800/298 |
| 2010/0035329 A1 | 2/2010 | Millis et al. | ................ | 435/254.2 |
| 2010/0120110 A1 | 5/2010 | Chappell | ........................ | 435/166 |
| 2010/0129306 A1 | 5/2010 | Julien et al. | ...................... | 424/65 |
| 2010/0151519 A1 | 6/2010 | Julien et al. | .................. | 435/69.1 |
| 2010/0151555 A1 | 6/2010 | Julien et al. | ................... | 435/193 |
| 2010/0216186 A1 | 8/2010 | Chappell et al. | ............. | 435/69.1 |
| 2011/0318797 A1 | 12/2011 | Chappell et al. | ............. | 435/155 |
| 2012/0129235 A1 | 5/2012 | Julien et al. | | |
| 2012/0196340 A1 | 8/2012 | Chappell et al. | ............. | 435/148 |

FOREIGN PATENT DOCUMENTS

| | | |
|---|---|---|
| EP | 0 768 381 | 4/1997 |
| WO | WO 94/22304 | 10/1994 |
| WO | WO 95/11913 | 5/1995 |
| WO | WO 96/36697 | 11/1996 |
| WO | WO 97/38571 | 10/1997 |
| WO | WO 97/38703 | 10/1997 |
| WO | WO 00/17327 | 3/2000 |
| WO | WO 02/72758 | 9/2002 |
| WO | WO 2004/031376 | 4/2004 |
| WO | WO 2006/014837 | 2/2006 |
| WO | WO 2006/079020 | 7/2006 |
| WO | WO 2010/019696 | 2/2010 |

OTHER PUBLICATIONS

Back and Chappell, J. Biol. Chem. 1995, vol. 270, pp. 7375-7481.*
EI Tamer et al. Arch. Biochem. and Biophys., 411 (2003) pp. 196-203.*
Schalk et al. PNAS, 97; (22): pp. 11948-11953.*
Dudareva N. et al., The Plant Cell, May 2003, vol. 15, p. 1227-1241.*
Erickson H. et al. J. Am. Chem. Soc.; 2003 vol. 125, pp. 6886-6888.*
Office Action, issued Jan. 8, 2009, in connection with corresponding U.S. Appl. No. 11/932,489 [13 pages].
Office Action, issued Oct. 23, 2009, in connection with corresponding U.S. Appl. No. 11/932,489 [11 pages].
Office Action, issued Mar. 2, 2011, in connection with corresponding Japanese Patent Application Serial No. Hei09-537218 [7 pages].
Alonso et al., "Purification of 4S-limonene synthase, a monoterpene cyclase from the glandular trichomes of peppermint (*Mentha x inperita*) and spearmint (*Mentha spicata*)," J. Biol. Chem. 267:7582-7587 (1992).

(Continued)

*Primary Examiner* — Russell Kallis
(74) *Attorney, Agent, or Firm* — McKenna Long & Aldridge LLP; Stephanie Seidman

(57) ABSTRACT

Provided is a chimeric isoprenoid synthase polypeptide including a first domain from a first isoprenoid synthase joined to a second domain from a second, heterologous, isoprenoid synthase, whereby the chimeric isoprenoid synthase is capable of catalyzing the production of isoprenoid reaction products that are not produced in the absence of the second domain of the second, heterologous, isoprenoid synthase. Also provided is a chimeric isoprenoid synthase polypeptide including an asymmetrically positioned heterologous domain, whereby the chimeric isoprenoid synthase is capable of catalyzing the production of isoprenoid reaction products that are not produced when the domain is positioned at its naturally-occurring site in the isoprenoid synthase polypeptide.

9 Claims, 9 Drawing Sheets

OTHER PUBLICATIONS

An et al., "Functional analysis of the 3' control region of the potato wound-inducible proteinase inhibitor II gene," Plant Cell 1:115-122 (1989).

An et al., "Organ-specific and developmental regulation of the nopaline synthase promoter in transgenic tobacco plants," Plant Physiol. 88:547-552 (1988).

Anderson et al., "Farnesyl diphosphate synthetase-molecular cloning sequence, and expression of an essential gene from *Saccharomyces cerevisiae*," J. Biol. Chem. 264(32):19176-19184 (1989).

Anke and Sterner, "Comparison of the antimicrobial and cytotoxic activities of twenty unsaturated sesquiterpene dialdehydes from plants and mushrooms," Planta Med. 57:344-346 (1991).

ATCC Accession No. CCL 61™, derived from CHO-K1 cell line, Depositor: Puck, T., Isolation date: 1957, Retrieved from the Internet: <URL:atcc.org/ATCCAdvancedCatalogSearch/ProductDetails/tabid/452/Default.aspx, (accessed Apr. 7, 2010; 4 pages).

ATCC Accession No. CRL 1650™, derived from CV-1 cell line, Cell type: SV40 transformed, Depositor: Gluzman, Y., Retrieved from the Internet: <URL:atcc.org/ATCCAdvancedCatalogSearch/ProductDetails/tabid/452/Defaultaspx, (accessed Apr. 7, 2010; 3 pages).

Ave et al., "Aphid repellant sesquiterpenes in glandular trichomes of *Solanum berthaulti* and *S. tuberosum*," Entomol. Exp. Appl. 44:131-138 (1987).

Back and Chappell, "Cloning and bacterial expression of a sesquiterpene cyclase from *Hyoscyamus muticus* and its molecular comparison to related terpene cyclases," J. Biol. Chem. 270:7375-7381 (1995).

Back and Chappell, "Identifying functional domains within terpene cyclases using a domain-swapping strategy," Proc. Natl. Acad. Sci. U.S.A. 93:6841-6845 (1996).

Back et al., "Expression of a plant sesquiterpene cyclase gene in *Escherichia coli*," Arch. Biochem. Biophys. 315:527-532 (1994).

Barnby and Klocke, "Effects of azadirachtin on levels of ecdysteroids and prothoracicotropic hormone-like activity in *Heliothis virescens* (Fabr.) larvae," J. Insect Physiol. 36:125-131 (1990).

Bio-Rad Technical Bulletin #1687, "Biolistic Particle Delivery Systems," Bio-Rad Laboratories, Hercules, California, pp. 1-11 (Feb. 9, 1996).

Bohlmann et al., "Terpenoid-based defenses in conifers: cDNA cloning, characterization, and functional expression of wound-inducible (E)-α-bisabolene synthase from grand fir (*Abies grandis*)," Proc. Natl. Acad. Sci. U.S.A. 95:6756-6761 (1993).

Borman, "Scientists mobilize to increase supply of anticancer drug taxol," Chem. Eng. News Sep. 1-18, 1991.

Bowers et al., "Sesquiterpene progenitor, germacrene A: an alarm pheromone in aphids," Science 196:680-681 (1976).

Bustos et al., "Regulation of β-glucuronidase expression in transgenic tobacco plants by an A/T-rich, *cis*-acting sequence found upstream of a French bean β-phaseolin gene," Plant Cell 1:839-853 (1989).

Callis et al., "Heat inducible expression of a chimeric maize hsp70CAT gene in maize protoplasts," Plant Physiol. 88:965-968 (1988).

Callis et al., "Introns increase gene expression in cultured maize cells," Genes Dev. 1:1183-1200 (1987).

Cane, D. and C. Pargellis, "Partial purification and characterization of pentalenene synthase," Arch. Biochem. Biophys. 254(2):421-429 (1987).

Cane et al., "Aristolochene biosynthesis and enzymatic cyclization of farnesyl pyrophosphate," J. Am. Chem. Soc. 111:8914-8916 (1989).

Cane et al., "Overexpression in *Escherichia coli* of soluble aristolochene synthase from *Penicillium roqueforti*," Arch. Biochem. Biophys. 302:415-419 (1993).

Cane et al., "Pentalenene synthase. Purification, molecular cloning, sequencing, and high-level expression in *Escherichia coli* of a terpenoid cyclase from *Streptomyces* UC5319," Biochem. 33:5846-5857 (1994).

Cane et al., "Trichodiene biosynthesis and the stereochemistry of the enzymatic cyclization of farnesyl pyrophosphate," Bioorg. Chem. 13:246-265 (1985).

Cane et al., "Trichodiene synthase. Identification of active site residues by site-directed mutagenesis," Biochem. 34:2480-2488 (1995).

Cane et al., "Trichodiene synthase. Substrate specificity and inhibition," Biochem. 34:2471-2479 (1995).

Cane, D., "Enzymatic formation of sesquiterpenes," Chem. Rev. 90:1089-1103 (1990).

Chappell, J. and R. Nable, "Induction of sesquiterpenoid biosynthesis in tobacco cell suspension cultures by fungal elicitor," Plant Physiol. 85:469-473 (1987).

Chappell et al., "Accumulation of capsidiol in tobacco cell cultures treated with fungal elicitor," Phytochem. 26:2259-2260 (1987).

Chappell et al., "Elicitor-inducible 3-hydroxy-3-methylglutaryl coenzyme A reductase activity is required for sesquiterpene accumulation in tobacco cell suspension cultures," Plant Physiol. 97:693-698 (1991).

Chappell et al., "Is the reaction catalyzed by 3-hydroxy-3-methylglutaryl coenzyme A reductase a rate-limiting step for isoprenoid biosynthesis in plants," Plant Physiol. 109:1337-1343 (1995).

Chappell, "Biochemistry and molecular biology of the isoprenoid biosynthetic pathway in plants," Annu. Rev. Plant Physiol. Plant Mol. Biol. 46:521-547 (1995).

Chappell, "The biochemistry and molecular biology of isoprenoid metabolism," Plant Physiol. 107:1-6 (1995).

Chen at al., "Cloning, expression and characterization of (+)-(δ-cadinene synthase: a catalyst for cotton phytoalexin biosynthesis," Arch. Biochem. Biophys. 324:255-266 (1995).

Chiu et al., "Engineered GFP as a vital reporter in plants," Curr. Biol. 6:325-330 (1996).

Colby et al., "4S-limonene synthase from the oil glands of spearmint (*Mentha spicata*). cDNA isolation, characterization, and bacterial expression of the catalytically active monoterpene cyclase," J. Biol. Chem. 268:23016-23024 (1993).

Corey et al., "Isolation of an *Arabidopsis thaliana* gene encoding cycloartenol synthase by functional expression in a yeast mutant lacking lanosterol synthase by the use of a chromatographic screen," Proc. Natl. Acad. Sci. U.S.A. 90:11628-11632 (1993).

Cortes et al., "Repositioning of a domain in a modular polyketide synthase to promote specific chain cleavage," Science 268:1487-1489 (1995).

Croteau et al., "Biosynthesis of monoterpenes: partial purification, characterization, and mechanism of action of 1,8-cineole synthase," Arch. Biochem. Biophys. 309:184-192 (1994).

Croteau et al., "Irreversible inactivation of monoterpene cyclases by a mechanism-based inhibitor," Arch. Biochem. Biophys. 307(2):397-404 (1993).

Croteau, R., "Evidence for the ionization steps in monoterpene cyclization reactions using 2-fluorogeranyl and 2-fluorolinalyl pyrophosphates as substrates," Arch. Biochem. Biophys. 251(2):777-782 (1986).

Degenhardt et al., "Monoterpene and sesquiterpene synthases and the origin of terpene skeletal biodiversity in plants," Phytochem. 70:1621-1637 (2009).

Dekeyser et al., "Transient gene expression in intact and organized rice tissues," Plant Cell 2:591-602 (1990).

Dixon et al., "Phytoalexin induction in French bean," Plant Physiol. 71:251-256 (1983).

Draper et al., "Ti plasmid homologous sequences present in tissues from *Agrobacterium* plasmid-transformed *Petunia* protoplasts," Plant Cell Physiol. 23:451-458 (1982).

Dudareva et al., "(E)-β-Ocimene and mycrene synthase genes of floral scent biosynthesis in snapdragon: function and expression of three terpene synthase genes of a new terpene synthase subfamily," Plant Cell 15:1227-1241 (2003).

Elakovich, S., "Sesquiterpenes as phytoalexins and allelopathic agents," Ecology and Metabolism of Plant Lipids 325:Chapter 7, pp. 93-108 (1986).

El-Feraly et al., "*Epi*-deoxyarteannuin B and 6,7-dehydroartemisinic acid from *Artemisia annua*," J. Nat. Prod. 52:196-198 (1989).

Enzell et al., "Mass spectra of tobacco isoprenoids," Mass Spectrom. Rev. 3:395 (1984).

Facchini and Chappell, "Gene family for an elicitor-induced sesquiterpene cyclase in tobacco," Proc. Natl. Acad. Sci. U.S.A. 89:11088-11092 (1992).

Fang et al., "Multiple cis regulatory elements for maximal expression of the cauliflower mosaic virus 35S promoter in transgenic plants," Plant Cell 1:141-150 (1989).

Freeman et al., "A comparison of methods for plasmid delivery into plant protoplasts," Plant Cell Physiol. 25(8):1353-1365 (1984).

Frohman et al., "Rapid production of full-length cDNAs from rare transcripts: amplification using a single gene-specific oligonucleotide primer," Proc. Natl. Acad. Sci. U.S.A. 85:8998-9002 (1988).

Fromm et al., "An octopine synthase enhancer element directs tissue-specific expression and binds ASF-1, a factor from tobacco nuclear extracts," Plant Cell 1:977-984 (1989).

Fromm et al., "Stable transformation of maize after gene transfer by electroporation," Nature 319:791-793 (1986).

Gambliel and Croteau, "Pinene cyclases I and II. Two enzymes from sage (Salvia officinalis) which catalyze sterospecific cyclizations of geranyl pyrophosphate to monoterpene olefins of opposite configuration," J. Biol. Chem. 259:740-748 (1984).

Garel, J., "Folding of Large Proteins: Multidomain and Multisubunit Proteins," in "Protein Folding," Creighton, ed., W.H. Freeman & Co., New York, pp. 406-407 (1992).

Gasser, C. and R. Fraley, "Genetically engineering plants for crop improvement," Science 244:1293-1299 (1989).

Gershenzon, J. and R. Croteau, in "Lipid Metabolism in Plants," Moore, T., ed., CRC Press, Boca Raton, Florida: CRC Press, pp. 340-388 (1993).

Gibson and Pickett, "Wild potato repels aphids by release of aphid alarm pheromone," Nature 302:608-609 (1983).

Goeddel et al., "Synthesis of human fibroblast interferon by E. coli," Nucleic Acids Res. 8(18):4057-4074 (1980).

Gordon-Kamm et al., "Transformation of maize cells and regeneration of fertile transgenic plants," Plant Cell 2:603-618 (1990).

Guo et al., "Biosynthesis of the diterpene cis-abienol in cell-free extracts of tobacco trichomes," Arch. Biochem. Biophys. 308:103-108 (1994).

Habtemariam et al., "A new antibacterial sesquiterpene from Premna oligotricha," J. Nat. Prod. 56:140-143 (1993).

Hanley, K. and J. Chappell, "Solubilization, partial purification, and immunodetection of squalene synthetase from tobacco cell suspension cultures," Plant Physiol. 98:215-220 (1992).

Hohn and Beremand, "Isolation and nucleotide sequence of a sesquiterpene cyclase gene from the trichothecene-producing fungus Fusarium sporotrichioides," Gene 79:131-138 (1989).

Hohn and Plattner, "Purification and characterization of the sesquiterpene cyclase aristolochene synthase from Penicillium roqueforti," Arch. Biochem. Biophys. 272:137-143 (1989).

Hohn and Vanmiddlesworth, "Purification and characterization of the sesquiterpene cyclase trichodiene synthetase from Fusarium sporotrichioides," Arch. Biochem. Biophys. 251:756-761 (1986).

Horsch et al., "A simple and general method for transferring genes into plants," Science 227:1229-1231 (1985).

Jong, J. and J. Sheen, "Sugar sensing in higher plants," Plant Cell 6:1665-1679 (1994).

Joly and Edwards, "Effect of site-directed mutagenesis of conserved aspartate and arginine residues upon farnesyl diphosphate synthase activity," J. Biol. Chem. 268:26983-26989 (1993).

Kalsi et al., "Stereostructures of two biologically active sesquiterpene lactones from Inula racemosa," Phytochem. 28:2093-2096 (1989).

Kay et al., "Duplication of CaMV 35S promoter sequences creates a strong enhancer for plant genes," Science 236:1299-1302 (1987).

Kindle, K., "High-frequency nuclear transformation of Chlamydomonas reinhardtii," Proc. Natl. Acad. Sci. U.S.A 87:1228-1232 (1990).

Koepp et al., "Cyclization of geranylgeranyl diphosphate to taxa-4(5),11(12)-diene is the committed step of taxol biosynthesis in Pacific Yew," J. Biol. Chem. 270:8686-8690 (1995).

Kubo et al., "Potentiation of antifungal activity of sesquiterpene dialdehydes against Candida albicans and two other fungi," Experientia 48:1162-1164 (1992).

Kuhlemeier et al., "The pea rbcS-3A promoter mediates light responsiveness but not organ specificity," Plant Cell 1:471-478 (1989).

Kurosaki, F., "Dissociation of dimeric 6-hydroxymellein synthase, a polyketide biosynthetic enzyme in carrot cell extracts, with loss of keto-reducing activity," Arch. Biochem. Biophys. 321(1):239-244 (1995).

Laskovics, F. and C. Poulter, "Prenyltransferase: determination of the binding mechanism and individual kinetic contsants for farnesylpyrophosphate synthetase by rapid quench and isotope partitioning experiments," Biochem. 20:1893-1901 (1981).

Lee et al., "Sesquiterpene antitumor agents: inhibitors of cellular metabolism," Science 196:533-536 (1977).

Lichtenstein, C. and S. Fuller, "Vectors for the genetic engineering of plants," in Genetic Engineering, vol. 6, Rigby P, ed., London, Academic Press, pp. 103-183 (1987).

Lichtenstein, C. and J. Draper, "Genetic engineering of plants," in DNA Cloning: A Practical Approach, vol. 2, pp. 67-119. Edited by D. Glover., Oxford & Washington D.C.: IRL Press (1985).

Mabry, T. and J. Gill, "Sesquiterpene lactones and other terpenoids," in "Herbivores: their interaction with secondary plant metabolites," Rosenthal and Janzen, eds., Academic Press, New York, pp. 502-537 (1979).

Marcotte et al., "Abscisic acid-responsive sequences from the Em gene of wheat," Plant Cell 1:969-976 (1989).

Mau, C. and C. West, "Cloning of casbene synthase cDNA: evidence for conserved structural features among terpenoid cyclases in plants," Proc. Natl. Acad. Sci. U.S.A. 91:8497-8501 (1994).

McDaniel et al., "Rational design of aromatic polyketide natural products by recombinant assembly of enzymatic subunits," Nature 375:549-554 (1995).

Midland et al., "The structure of syringolides 1 and 2, novel C-glycosidic elicitors from Pseudomonas syringae pv. tomato," J. Org. Chem. 58:2940-2945 (1993).

Moesta and West, "Casbene synthetase: regulation of phytoalexin biosynthesis in Ricinus communis L. seedlings: purification of casbene synthetase and regulation of its biosynthesis during elicitation," Arch. Biochem. Biophys. 238:325-333 (1985).

Munck and Croteau, "Purification and characterization of the sesquiterpene cyclase patchoulol synthase from Pogostemon cablin," Arch. Biochem. Biophys. 282:58-64 (1990).

Noel, J. and M. Tsai, "Phospholipase $A_2$ engineering: design, synthesis, and expression of a gene for bovine (pro)phospholipase $A_2$," J. Cell. Biochem. 40:309-320 (1989).

Odell et al., "Identification of DNA sequences required for activity of the cauliflower mosaic virus 25S promoter," Nature 313:810-812 (1985).

Ohnuma et al., "A role of the amino acid residue located on the fifth position before the first aspartate-rich motif of farnesyl diphosphate sythase of determination of the final product," J. Biol. Chem. 271(48):30748-30754 (1996).

Ow et al., "Functional regions of the cauliflower mosaic virus 35S RNA promoter determined by use of the firefly luciferase gene as a reporter of promoter activity," Proc. Natl. Acad. Sci. U.S.A. 84:4870-4874 (1987).

Potrykus, I., "Gene transfer to plants: assessment of published approaches and results," Annu. Rev. Plant Physiol. Plant Mol. Biol. 42:205-225 (1991).

Proctor, R. and T. Hohn, "Aristolochene synthase. Isolation, characterization, and bacterial expression of a sesquiterpenoid biosynthetic gene (Ari1) from Penicillin roqueforti," J. Biol. Chem. 268(8):4543-4548 (1993).

Pyun et al., "Regiospecificity and isotope effects associated with the methyl-methylene elimination in the enzyme-catalyzed biosynthesis of (R)- and (S)-limonene," J. Org. Chem. 58:3998-4009 (1993).

Rajaonarivony et al., "Characterization and mechanism of (4S)-limonene synthase, a monoterpene cyclase from the glandular trichomes of peppermint (Mentha x piperita)," Arch. Biochem. Biophys. 296(1):49-57 (1992).

Rajaonarivony et al., "Evidence for an essential histidine residue in 4S-limonene synthase and other terpene cyclases," Arch. Biochem. Biophys. 299(1):77-82 (1992).

Rosahl et al., "Expression of a tuber-specific storage protein in transgenic tobacco plants: demonstration of an esterase activity," EMBO J. 6(5):1155-1159 (1987).

Russell et al., "A sesquiterpenoid ant repellant from Dysoxylum spectabile," Phytochem. 35:1455-1456 (1994).

Ruzicka, L., "The isoprene rule and the biogenesis of terpenic compounds," Experientia 10:357-367 (1953).

Savage et al., "Monoterpene synthases of *Pinus contorta* and related conifers," J. Biol. Chem. 269:4012-4020 (1994).

Schäffner, A. and J. Sheen, "Maize *rbcS* promoter activity depends on sequence elements not found in dicot *rbcS* promoters," Plant Cell 3:997-1012 (1991).

Schalk, M. and R. Croteau, "A single amino acid substitution (F363I) converts the regiochemistry of the spearmint (-)-limonene hydroxylase from a C6- to a C3-hydroxylase," Proc. Natl. Acad. Sci. U.S.A. 97(22):11948-11953 (2000).

Schernthaner et al., "Endosperm-specific activity of a zein gene promoter in transgenic tobacco plants," EMBO J. 7(5):1249-1255 (1988).

Sheen et al., "Green-fluorescent protein as a new vital marker in plant cells," Plant J. 8(5):777-784 (1995).

Sheen, J., "Metabolic repression of transcription in higher plants," Plant Cell 2:1027-1038 (1990).

Shen, Q. and T. Ho, "Functional dissection of an abscisic acid (ABA)-inducible gene reveals two independent ABA-responsive complexes each containing a G-box and a novel *cis*-acting element," Plant Cell 7:295-307 (1995).

Shimatake, H. and M. Rosenberg, "Purified λ regulatory protein *c*II positively activates promoters for lysogenic development," Nature 292:128-132 (1981).

Siebertz et al., "*cis*-Analysis of the wound-inducible promoter *wun1* in transgenic tobacco plants and histochemical localization of its expression," Plant Cell 1:961-968 (1989).

Simpson et al., "Light-inducible and tissue-specific expression of a chimaeric gene under control of the 5'-flanking sequence of a pea chlorophyll *a/b*-binding protein gene," EMBO J. 4(11):2723-2729 (1985).

Smith et al., "The syringolides: bacterial C-glycosyl lipids that trigger plant disease resistance," Tet. Lett. 34:223-226 (1993).

Song, L. and C. Poulter, "Yeast farnesyl-diphosphate synthase: site-directed mutagenesis of residues in highly conserved prenyltransferase domains I and II," Proc. Natl. Acad. Sci. U.S.A. 91:3044-3048 (1994).

Stevens, "Biological Activity and Chemistry of Sesquiterpene Lactones," in "Sesquiterpene Lactones," pp. 65-80 (1984).

Stevens, K., in "Isopentoids in Plants, Biochemistry and Function," Nes et al., eds., New York, NY., Marcel Dekker, pp. 65-80 (1984).

Stoessl et al., "Sesquiterpenoid stress compounds of the solanaceae," Phytochem. 15:855-872 (1976).

Straub et al., "Structure and promoter analysis of an ABA- and stress-regulated barley gene, HVA1," Plant Mol. Biol. 6:617-630 (1994).

Takahashi, T. and Y. Komeda, "Characterization of two genes encoding small heat-shock proteins in *Arabidopsis thaliana*," Mol. Gen. Genet. 219:365-372 (1989).

Takahashi et al., "Isolation and analysis of the expression of two genes from the 81-kilodalton heat-shock proteins from *Arabidopsis*," Plant Physiol. 99:383-390 (1992).

Tarshis et al., "Regulation of product chain length by isoprenyl diphosphate synthases," Proc. Natl. Acad. Sci. U.S.A. 93:15018-15023 (1996).

Terada, R. and K. Shimamoto, "Expression of CaMV35S-GUS gene in transgenic rice plants," Mol. Gen. Genet. 220:389-392 (1990).

Thornburg et al., "Wound-inducible expression of a potato inhibitor II-chloramphenicol acetyltransferase gene fusion in transgenic tobacco plants," Proc. Natl. Acad. Sci. U.S.A. 84:744-748 (1987).

Visser et al., "Expression of a chimaeric granule-bound starch synthase-GUS gene in transgenic potato plants," Plant Mol. Biol. 17:691-699 (1991).

Vögeli, U. and J. Chappell, "Induction of sesquiterpene cyclase and suppression of squalene synthetase activities in plant cell cultures treated with fungal elicitor," Plant Physiol. 88:1291-1296 (1988).

Vögeli, U. and J. Chappell, "Inhibition of a plant sesquiterpene cyclase by mevinolin," Arch. Biochem. Biophys. 288(1):157-162 (1991).

Vögeli, U. and J. Chappell, "Regulation of a sesquiterpene cyclase in cullulase-treated tobacco cell suspension cultures," Plant Physiol. 94:1860-1866 (1990).

Vögeli et al., "Inhibition of phytoalexin biosynthesis in elicitor-treated tobacco cell-suspension cultures by calcium/calmodulin antagonists," Plant Physiol. 100:1369-1376 (1992).

Vögeli et al., "Purification and characterization of an inducible sesquiterpene cyclase from elicitor-treated tobacco cell suspension cultures," Plant Physiol. 93:182-187 (1990).

Weichselbraun et al., "Definition of the human immunodeficiency virus type 1 Rev and human T-cell leukemia virus type I Rex protein activation domain by functional exhange," J. Virol. 66(4):2583-2587 (1992).

Wheeler, C. and R. Croteau, "Direct demonstration of the isomerization component of the monoterpene cyclase reaction using a cyclopropylcarbinyl pyrophosphate substrate analog," Proc. Natl. Acad. Sci. U.S.A. 84:4856-4859 (1987).

Whitehead et al., "5-epi-Aristolochene is a common precursor of the sesquiterpene phytoalexins capsidiol and debneyol," Phytochemistry 28(3):775-779 (1989).

Whitehead et al., "Synthesis of (+)-5-epi-aristolochene and (+)-1-deoxycapsidiol from capsidiol," Phytochemistry 29(2):479-482 (1990).

Wildung, M. and R. Croteau, "A cDNA clone for taxadiene synthase, the diterpene cyclase that catalyzes the committed step of taxol biosynthesis," J. Biol. Chem. 271(16):9201-9204 (1996).

Wong et al., "Domain exchange: characterization of a chimeric lipase of hepatic lipase and lipoprotein lipase," Proc. Natl. Acad. Sci. U.S.A. 88:11290-11294 (1991).

Zhang, W. and R. Wu, "Efficient regeneration of transgenic plants from rice protoplasts and correctly regulated expression of the foreign gene in the plants," Theor. Appl. Genet. 76:835-840 (1988).

Zook et al., "Characterization of novel sesquiterpene biosynthesis in tobacco expressing fungal sesquiterpenoid synthase," Plant Physiol. 112:311-318 (1996).

Office Action, issued Jul. 30, 2003, in connection with U.S. Appl. No. 09/514,513.

Office Action, issued Feb. 10, 2005, in connection with U.S. Appl. No. 09/514,513.

Office Action, issued Feb. 9, 2006, in connection with U.S. Appl. No. 09/514,513.

Office Action, issued Aug. 6, 2002, in connection with U.S. Appl. No. 09/576,057.

Office Action, issued Feb. 27, 2003, in connection with U.S. Appl. No. 09/576,057.

Office Action, issued Dec. 13, 2006, in connection with U.S. Appl. No. 10/717,500.

Office Action, issued Mar. 6, 2008, in connection with U.S. Appl. No. 10/717,500.

Office Action, issued Sep. 30, 2008, in connection with U.S. Appl. No. 10/717,500.

Office Action, issued Jun. 1, 2009, in connection with U.S. Appl. No. 10/717,500.

Office Action, issued Jan. 5, 2010, in connection with U.S. Appl. No. 10/717,500.

International Search Report, issued Aug. 8, 1997, in connection with International Patent Application Serial No. PCT/US97/05986.

Examiner's Report, issued Jul. 21, 2003, in connection with Canadian Patent Application Serial No. 2,250,712.

Response to Examination Report, filed Jan. 21, 2004, in connection with Canadian Patent Application Serial No. 2,250,712.

Examiner's Report, issued Dec. 10, 2004, in connection with Canadian Patent Application Serial No. 2,250,712.

Response to Examination Report, filed Jan. 18, 2005, in connection with Canadian Patent Application Serial No. 2,250,712.

Official Action, issued Feb. 16, 2004, in connection with Czech Republic Patent Application Serial No. 1998-3179.

Response to Official Action, filed Apr. 12, 2004, in connection with Czech Republic Patent Application Serial No. 1998-3179.

Examination Report, issued Sep. 20, 1999, in connection with European Patent Application Serial No. 97921142.2.
Response to Examination Report, filed Jan. 20, 2000, in connection with European Patent Application Serial No. 97921142.2.
Examination Report, issued Apr. 7, 2000, in connection with European Patent Application Serial No. 97921142.2.
Response to Examination Report, filed Oct. 12, 2000, in connection with European Patent Application Serial No. 97921142.2.
Summary of Telephone Consultation with Examiner, issued Nov. 30, 2000, in connection with European Patent Application Serial No. 97921142.2.
Response to Telephone Consultation with Examiner, filed Mar. 29, 2001, in connection with European Patent Application Serial No. 97921142.2.
European Search Report, issued Aug. 28, 2002, in connection with European Patent Application Serial No. 02009895.
Official Action, issued Aug. 22, 2006, in connection with Japanese Patent Application Serial No. 09-537218.
Response to Official Action, filed Feb. 21, 2007, in connection with Japanese Patent Application Serial No. 09-537218.
Official Action, issued Mar. 11, 2008, in connection with Japanese Patent Application Serial No. 09-537218.
Appeal Brief, filed Jul. 3, 2008, in connection with Japanese Patent Application Serial No. 09-537218.
Official Action, issued Jun. 30, 2003, in connection with Polish Patent Application Serial No. P.329 404.
Response to Official Action, filed Aug. 13, 2003, in connection with Polish Patent Application Serial No. P.329 404.
Official Action, issued Nov. 27, 2003, in connection with Polish Patent Application Serial No. P.329 404.
Response to Official Action, filed Feb. 9, 2004, in connection with Polish Patent Application Serial No. P.329 404.
Official Action, issued May 20, 2004, in connection with Polish Patent Application Serial No. P.329 404.
Response to Official Action, filed Jun. 30, 2004, in connection with Polish Patent Application Serial No. P.329 404.
Official Action, issued Dec. 2, 2004, in connection with Polish Patent Application Serial No. P.329 404.
Allylix, "Protein engineering and chembiosynthesis to produce novel sesquiterpenoids," Presentation at BIO World Congress on Industrial Biotechnology & Bioprocessing, Washington, D.C. (Jun. 28, 2010).
Back et al., "Cloning and bacterial expression of sesquiterpene cyclase, a key branch point enzyme for the synthesis of sesquiterpenoid phytoalexin capsidiol in UV-challenged leaves of *Capsicum annuum*," Plant Cell. Physiol. 39:899-904 (1998).
Back et al., "Cloning of a sesquiterpene cyclase and its functional expression by domain swapping strategy," Mol. Cells 10:220-225 (2000).
Chappell, "The genetics and molecular genetics of terpene and sterol origami," Curr. Opin. Plant Biol. 5:151-157 (2002).
Deguerry et al., "The diverse sesquiterpene profile of patchouli, *Pogostemon cablin*, is correlated with a limited number of sesquiterpene synthases," Arch. Biochem. Biophys. 454:123-136 (2006).
Devarenne et al., "Molecular characterization of tobacco squalene synthase and regulation in response to fungal elicitor," Arch. Biochem. Biophys. 349:205-215 (1998).
Devarenne et al., "Regulation of squalene synthase, a key enzyme of sterol biosynthesis, in tobacco," Plant Physiol. 129:1095-1106 (2002).
Greenhagen and Chappell, "Molecular scaffolds for chemical wizardry: learning nature's rules for terpene cyclases," Proc. Natl. Acad. Sci. U.S.A. 98:13479-13491 (2001).
Greenhagen et al., "Probing sesquiterpene hydroxylase activities in a coupled assay with terpene synthases," Arch. Biochem. Biophys. 409:385-394 (2003).
Greenhagen et al., "Identifying and manipulating structural determinates linking catalytic specificities in terpene synthases," Proc. Natl. Acad. Sci. U.S.A. 103:9826-9831 (2006).
Lee and Chappell, "Biochemical and genomic characterization of terpene synthases in *Magnolia grandiflora*," Plant Physiol. 147:1017-1033 (2008).

Mandujano-Chavez et al., "Differential induction of sesquiterpene metabolism in tobacco cell suspension cultures by methyl jasmonate and fungal elicitor," Arch. Biochem. Biophys. 381:285-294 (2000).
Mathis et al., "Pre-steady-state study of recombinant sesquiterpene cyclases," Biochem. 36:8340-8348 (1997).
Nah et al., "Partial characterization of farnesyl and geranylgeranyl diphosphatases induced in rice seedlings by UV-C irradiation," Plant Cell Physiol. 42:864-867 (2001).
Newman et al., "Characterization of the TAC box, a cis-element within a elicitor-inducible sesquiterpene cyclase promoter," Plant J. 16:1-12 (1998).
Newman and Chappell, "Isoprenoid biosynthesis in plants: carbon partitioning within the cytoplasmic pathway," Crit. Rev. Biochem. Mol. Biol. 34:95-106 (1999).
Okada et al., "Molecular characterization of squalene synthase from the green microalga *Botryococcus braunii*, race B," Arch. Biochem. Biophys. 373:307-317 (2000).
Okada et al., "Characterization of botryococcene synthase enzyme activity, a squalene synthase-like activity from the green microalga *Botryococcus braunii*, race B," Arch. Biochem. Biophys. 422:110-118 (2004).
O'Maille et al., "A single-vial analytical and quantitative gas chromatography-mass spectrometry assay for terpene synthases," Anal. Biochem. 335:210-217 (2004).
O'Maille et al., "Biosynthetic potential of sesquiterpene synthases: alternative products of tobacco 5-epi-aristolochene synthase," Arch. Biochem. Biophys. 448:73-82 (2006).
Ralston, L., Kwan, S., Chappell, J. "Biochemical and molecular characterization of 5-epi-aristolochene 3-hydroxylase, a putative regulatory enzyme in the biosynthesis of sesquiterpene phytoalexins in tobacco," Plant Interactions with Other Organisms. Annual Meeting of the American Society of Plant Physiologists. Madison, WI., Jun. 27-Jul. 1, 1998, Session 47:Abstract #737 (Poster Presentation).
Ralston et al., "Cloning, heterologous expression, and fuctional characterization of 5-epi-aristolochene-1,3-dihydroxylase from tobacco (*Nicotiana tabacum*)," Arch. Biochem. Biophys. 393:222-235 (2001).
Rising et al., "Demonstration of germacrene A as an intermediate in 5-epi-aristolochene synthesis catalysis," J. Am. Chem. Soc. 122:1861-1866 (2000).
Schenk et al., "Stereochemistry and deuterium isotope effects associated with the cyclization-rearrangements catalyzed by tobacco epiaristolochene and hyoscyamus premnaspirodiene synthases, and the chimeric CH4 hybrid cyclase," Arch. Biochem. Biophys. 448:31-44 (2006).
Starks et al., "Structural basis for cyclic terpene biosynthesis by tobacco 5-epi-aristolochene synthase," Science 277:1815-1820 (1997).
Takahashi et al., "Kinetic and molecular analysis of 5-epiaristolochene 1,3-dihydroxylase, a cytochrome P450 enzyme catalyzing successive hydroxylations of sesquiterpenes," J. Biol. Chem. 280:3686-3696 (2005).
Takahashi et al., "Functional characterization of premnaspirodiene oxygenase, a cytochrome P450 catalyzing regio- and stereo-specific hydroxylations of diverse sesquiterpene substrates," J. Biol. Chem. 43:31744-31754 (2007).
Takahasi et al., "Metabolic engineering of sesquiterpene metabolism in yeast," Biotechnol. Bioeng. 97:170-181 (2007).
Thai et al., "Farnesol is utilized for isoprenoid biosynthesis in plant cells via farnesyl pyrophosphate formed by successive monophosphorylation reactions," Proc. Natl. Acad. Sci. U.S.A. 96:13080-13085 (1999).
Wu et al., "Surrogate splicing for functional analysis of sesquiterpene synthase genes," Plant Physiol. 138:1322-1333 (2005).
Wu et al., "Redirection of cytosolic or plastidic isoprenoid precursors elevates terpene production in plants," Nat. Biotechnol. 24:1441-1447 (2006).
Yin et al., "Regulation of sesquiterpene cyclase gene expression—characterization of an elicitor- and pathogen-inducible promoter," Plant Physiol. 115:437-451 (1997).
Zhao et al., "Eremophilane sesquiterpenes from capsidiol," J. Org. Chem. 69:7428-7435 (2004).
U.S. Appl. No. 12/540,094, filed Aug. 12, 2009.

U.S. Appl. No. 12/540,050, filed Aug. 12, 2009.
U.S. Appl. No. 10/717,500, filed Nov. 21, 2003.
U.S. Appl. No. 12/182,000, filed Jul. 29, 2008.
U.S. Appl. No. 12/259,497, filed Oct. 28, 2008.
U.S. Appl. No. 12/579,232, filed Oct. 14, 2009.
U.S. Appl. No. 13/317,839, filed Oct. 28, 2011.
U.S. Appl. No. 13/261,101, filed Dec. 22, 2011.
U.S. Appl. No. 13/199,349, filed Aug. 26, 2011.

* cited by examiner

| | | Hinc II | | | | DOMINANT REACTION PRODUCTS [a] | | SPECIFIC ACTIVITY |
|---|---|---|---|---|---|---|---|---|
| | | HindIII | NdeI | Xba 1 342 | Cla 1 | Xba 1 532 | TEAS SPECIFIC | HVS SPECIFIC | nmol/mg prot•h |
| $NH_3^+$ TEAS | | 152 | 281 | 379 | 442 | $COO^-$ 548 aa | 100% | - | 47 |
| HVS | | HindIII 160 | NdeI 268 | | | $COO^-$ 566 aa | - | 100 | 28 |
| CH 1 | HindIII / TEAS / HVS | | | | | | - | 100 | 35 |
| CH 2 | NdeI | | | | | | - | 100 | 22 |
| CH 3 | Cla 1 | | | | | | 100 | - | 21 |
| CH 4 | Hinc II | | | | | | 66 | 34 | 40 |
| CH 5 | HindIII | | | | | | 100 | - | 3 |
| CH 6 | HindIII / Cla 1 | | | | | | 100 | 0 | 27 |
| CH 7 | NdeI | | | | | | NO ENZYME ACTIVITY | | - |
| CH 8 | NdeI / Cla 1 | | | | | | NO ENZYME ACTIVITY | | - |
| CH 9 | HindIII / NdeI | | | | | | - | 100 | 63 |
| CH 10 | Hind III / Hinc II | | | | | | 68 | 34 | 25 |
| CH 11 | NdeI / Hinc II | | | | | | 61 | 39 | 28 |
| CH 12 | Hinc II / Cla 1 | | | | | | 73 | 27 | 27 |
| CH 13 | Xba 1 | | | | | | 23 | 77 | 60 |
| CH 14 | NdeI Xba 1 | | | | | | 33 | 67 | 37 |

Fig. 4A

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Synthesized

<400> SEQUENCE: 1
gggatcgatg acatagccac gtatgaggtt 30

<210> SEQ ID NO 2
<211> LENGTH: 17
<212> TYPE: DNA
<213> ORGANISM: Artificial Sequence
<220> FEATURE:
<223> OTHER INFORMATION: Synthesized

<400> SEQUENCE: 2
aatacgactc actatag 17

<210> SEQ ID NO 3
<211> LENGTH: 27
<212> TYPE: DNA
<213> ORGANISM: Artificial Sequence
<220> FEATURE:
<223> OTHER INFORMATION: Synthesized

<400> SEQUENCE: 3
cgagtcaaca tggtttattg agggata 27

<210> SEQ ID NO 4
<211> LENGTH: 28
<212> TYPE: DNA
<213> ORGANISM: Artificial Sequence
<220> FEATURE:
<223> OTHER INFORMATION: Synthesized

<400> SEQUENCE: 4
tattctagat ctctatgacg attatgaa 28

```
<210> SEQ ID NO 5
<211> LENGTH: 42
<212> TYPE: DNA
<213> ORGANISM: Artificial Sequence
<220> FEATURE:
<223> OTHER INFORMATION: Synthesized

<400> SEQUENCE: 5
gggagctcga attccatggc ctcagcagca gttgcaaact at            42

<210> SEQ ID NO 6
<211> LENGTH: 30
<212> TYPE: DNA
<213> ORGANISM: Artificial Sequence
<220> FEATURE:
<223> OTHER INFORMATION: Synthesized

<400> SEQUENCE: 6
gggatcgata actctgcata atgtagcatt                          30
```

CHIMERIC ISOPRENOID SYNTHASES AND USES THEREOF

CROSS-REFERENCE TO RELATED APPLICATIONS

This application is a continuation of U.S. Ser. No. 11/932,489, filed Oct. 31, 2007 now abandoned, which is a continuation of U.S. Ser. No. 10/717,500, filed Nov. 21, 2003, which is a continuation of U.S. Ser. No. 09/514,513, filed Feb. 28, 2000 (now U.S. Pat. No. 7,186,891), which is a divisional of U.S. Ser. No. 09/134,699, filed Aug. 14, 1998 (now U.S. Pat. No. 6,072,045), which is a continuation of U.S. Ser. No. 08/631,341, filed Apr. 12, 1996 (now U.S. Pat. No. 5,824,774).

STATEMENT AS TO FEDERALLY SPONSORED RESEARCH

This invention was made in part with Government funding, and the Government therefore has certain rights in the invention.

BACKGROUND OF THE INVENTION

This invention relates to modified isoprenoid synthase enzymes, their encoding genes, and uses thereof.

The term isoprenoid is used to refer to a family of compounds derived from the isoprene building block. In particular, plant isoprenoids comprise a structurally diverse group of compounds that can be divided into classes of primary and secondary metabolites (FIG. 1). Isoprenoids that are primary metabolites include sterols, carotenoids, growth regulators, and the polyprenol substituents of dolichols, quinones, and proteins. These compounds are essential for membrane integrity, photoprotection, orchestration of developmental programs, and anchoring essential biochemical functions to specific membrane systems, respectively. Isoprenoids that are classified as secondary metabolites include monoterpenes, sesquiterpenes, and diterpenes. These compounds are said to mediate important interactions between plants and their environment. For example, specific terpenoids have been correlated with plant-plant (Stevens, In: *Isopentoids in Plants*, Nes, W. D. Fuller, G., and Tsai, L.-S., eds., Marcel Dekker, New York, pp. 65-80, 1984), plant-insect (Gibson and Pickett, *Nature* 302:608, 1983), and plant-pathogen interactions (Stoessl et al., *Phytochemistry* 15:855, 1976).

The common denominator for this diverse array of compounds is their universal five-carbon building block, isoprene. The "biogenic isoprene rule" was employed to rationalize the biosynthetic origins of all terpenoids derived from isoprene (Ruzicka, *Experientia* 10:357, 1953). The polymerization of two diphosphorylated isoprene building blocks (e.g., IPP and dimethylallyl) generates geranyl diphosphate (GPP), a linear C10 intermediate that can be converted to cyclic or linear end-products representing the monoterpenes, or used in another round of polymerization. The addition of a third isoprene unit to GPP generates farnesyl diphosphate (FPP), which can also be converted to cyclic or linear products representing the sesquiterpene class. Continuing the polymerization and chemical differentiation cycle leads to the production of other classes of terpenoids named according to the number of isoprene building blocks leading to their biosynthesis, for example, the addition of a third IPP to FPP generates geranylgeranyl diphosphate (GGPP).

These polymerization reactions are catalyzed by prenyltransferases that direct the attack of a carbocation (an electron deficient carbon atom resulting from the loss of the diphosphate moiety of one substrate) to an electron-rich carbon atom of the double bond on the IPP molecule (FIG. 2). The electrophilic nature of these reactions is said to be unusual relative to more general nucleophilic condensation reactions, but this appears to be a common reaction among isoprenoid biosynthetic enzymes and especially those enzymes involved in catalyzing the cyclization of various isoprenoid intermediates (Gershenzon and Croteau, In: *Lipid Metabolism in Plants*, Moore, T. S., ed., CRC Press, Boca Raton, Fla., pp. 340-388). The enzymes responsible for the cyclization of GPP, FPP, and GGPP are referred to as monoterpene, sesquiterpene, and diterpene synthases or synthases, and represent reactions committing carbon from the general isoprenoid pathway to end products in the monoterpene, sesquiterpene, and diterpene classes, respectively.

Two important biochemical distinctions between the prenyltransferase and synthase reactions are illustrated in FIG. 2. The prenyltransferases catalyze carbon carbon bond formation between two substrate molecules, whereas the synthases catalyze an intramolecular carbon-carbon bond formation. The prenyltransferases also catalyze reactions with very little variance in the stereochemistry or length of the ensuing polymer. Prenyltransferases differ in the length of the allyic substrates that can be accepted in initiating these reactions. The synthases are also substrate specific. However, diverse sesquiterpene synthases, for example, can utilize the same substrate to produce different reaction products.

The biosynthesis of isoprenoids such as cyclic terpenes is said to be determined by key branch point enzymes referred to as terpene synthases. The reactions catalyzed by terpene synthases are complex, intramolecular cyclizations that may involve several partial reactions. For example, the bioorganic rationale for the cyclization of FPP by two sesquiterpene synthases are shown in FIG. 3. In step 1, the initial ionization of FPP is followed by an intramolecular electrophillic attack between the carbon bearing the diphosphate moiety and the distal double bond to form germacene A, a macrocyclic intermediate. Internal ring closure and formation of the eudesmane carbonium ion constitutes step 2. For tobacco 5-epi-aristolochene synthase (TEAS), the terminal step is a hydride shift, methyl migration, and deprotonation at C9 giving rise to 5-epi-aristolochene as depicted in step 3a. *Hyoscyamus muticus* vetispiradiene synthase (HVS) shares a common mechanism at steps 1 and 2, but differs from TEAS in the third partial reaction in which a ring contraction would occur due to alternative migration of an electron pair. In each case, a monomeric protein of approximately 64 kD catalyzes the complete set of partial reactions and requires no cofactors other than $Mg^{+2}$.

SUMMARY OF THE INVENTION

In general, the invention features a chimeric isoprenoid synthase polypeptide including a first domain from a first isoprenoid synthase joined to a second domain from a second, heterologous isoprenoid synthase, whereby the chimeric isoprenoid synthase is capable of catalyzing the production of isoprenoid reaction products that are not produced in the absence of the second domain of the second, heterologous isoprenoid synthase. In preferred embodiments, the chimeric isoprenoid synthase is capable of catalyzing at least two different isoprenoid reaction products; the isoprenoid reaction products are cyclic; the second domain of the second, heterologous isoprenoid synthase also determines the ratio of the isoprenoid reaction products of the chimeric isoprenoid synthase; the first domain from the first isoprenoid synthase is a plant isoprenoid synthase and the second domain from the second, heterologous isoprenoid synthase is also from a plant isoprenoid synthase.

Preferably, the chimeric isoprenoid synthase is chosen from the group consisting of (a) the tobacco-*Hyoscyamus* CH4 chimeric isoprenoid synthase; (b) the tobacco-*Hyoscyamus* CH10 chimeric isoprenoid synthase; (c) the tobacco-*Hyoscyamus* CH11 chimeric isoprenoid synthase; (d) the tobacco-*Hyoscyamus* CH12 chimeric isoprenoid synthase; (e) the tobacco-*Hyoscyamus* CH13 chimeric isoprenoid synthase; or (f) the tobacco-*Hyoscyamus* CH14 chimeric isoprenoid synthase, all as described herein.

In preferred embodiments, the chimeric isoprenoid synthase catalyzes the production of an isoprenoid reaction product that is of agricultural, pharmaceutical, commercial, or industrial significance (e.g., an antifungal agent, antibacterial agent, or antitumor agent).

In other related aspects, the invention features DNA, vectors, and cells (for example, *E. coli, Saccharomyces cerevisiae*, animal or plant cells) encoding or containing a chimeric isoprenoid synthase polypeptide.

In another aspect, the invention features a chimeric isoprenoid synthase polypeptide including an asymmetrically positioned homologous domain whereby the chimeric isoprenoid synthase is capable of catalyzing the production of isoprenoid reaction products (preferably, cyclic products) when the domain is positioned at its naturally-occurring site in the isoprenoid synthase polypeptide.

In another aspect, the invention features a method for producing a chimeric isoprenoid synthase polypeptide, the method involving: (a) providing a cell transformed with DNA encoding a chimeric isoprenoid synthase positioned for expression in the cell; (b) culturing the transformed cell under conditions for expressing the DNA; and (c) recovering the chimeric isoprenoid synthase.

By "isoprenoid synthase" is meant a polypeptide that is capable of catalyzing a reaction involving the intramolecular carbon-carbon bond formation of an allylic diphosphate substrate (for example, a $C_{10}$, $C_{15}$, or $C_{20}$ allylic diphosphate substrate) to an isoprenoid product (for example, a monoterpene, diterpene, sesquiterpene, or sterol product). Examples of such isoprenoid synthases include, without limitation, monoterpene synthases (for example, limonene synthase), diterpene synthases (for example, casbene synthase), and sesquiterpene synthases (for example, 5-epi-aristolochene synthase, vetispiradiene synthase, and cadinene synthase) that are responsible for cyclization of geranyl diphosphate (GPP), farnesyl diphosphate (FPP), and geranylgeranyl diphosphate (GGPP), respectively. A number of terpene synthases from plant and microbial sources have been isolated and characterized (see, for example, Moestra and West, *Arch. Biochem. Biophys.* 238:325, 1985; Hohn and Van Middlesworth, *Arch. Biochem. Biophys.* 251:756, 1986; Hohn and Plattner, *Arch. Biochem. Biophys.* 272:137, 1989; Cane and Pargellis, *Arch. Biochem. Biophys.* 254:421, 1987; Munck and Croteau, *Arch. Biochem. Biophys.* 282:58, 1990; Alonso et al., *J. Biol. Chem.* 267:7582, 1992; Savage et al., *J. Biol. Chem.* 269:4012, 1994; Croteau et al., *Arch. Biochem. Biophys.* 309:184, 1994; Vogeli et al., *Plant Physiol.* 93:182, 1990; Guo et al., *Arch. Biochem. Biophys.* 308:103, 1994; and Gambliel and Croteau, *J Biol. Chem.* 259:740, 1984). In general, terpene synthases are soluble enzymes having a molecular weight of about 40 to 100 kD. Genes encoding a number of monoterpene, diterpene, and sesquiterpene synthases have been described for a number of plant and microbial organisms (see, for example, Hohn and Beremand, *Gene* 79:131, 1989; Proctor and Hohn, *J Biol. Chem.* 268:4543, 1993; Facchini and Chappell, *Proc. Natl. Acad. Sci.* 89:11088, 1992; Back and Chappell, *J Biol. Chem.* 270:7375, 1995; Colby et al., *J. Biol. Chem.* 268:23016, 1993; Mau and West, *Proc. Natl. Acad. Sci.* 91:8497, 1994; Chen et al., *Arch. Biochein. Biophys.* 324:255, 1994; and Cane et al., Biochemistry 33:5846, 1994).

By "polypeptide" or "protein" is meant any chain of amino acids, regardless of length or post-translational modification (for example, glycosylation or phosphorylation).

By "joined to" is meant covalently bonded either directly or indirectly (i.e., the domains are separated by an intervening amino acid sequence). Such domains may be bonded by any means, including, without limitation, a peptide bond or chemical linkage.

By "domain" is meant a contiguous stretch of amino acids within a polypeptide or protein.

By "isoprenoid" is meant a compound that is derived from an isoprene building block. In particular, isoprenoid compounds include, without limitation, monoterpenes, diterpenes, sesquiterpenes, and sterols. As described herein, isoprenoids are found in a variety of organisms, for example, animal, fungal, or bacterial sources.

By "asymmetrically positioned" is meant located within the chimeric polypeptide at a site which differs from its position in the naturally-occurring polypeptide.

By "heterologous" is meant derived from different sources (in this case, different polypeptides).

By "homologous" is meant derived from the same source (in this case, the same polypeptide).

Other features and advantages of the invention will be apparent from the following description of the preferred embodiments thereof, and from the claims.

DETAILED DESCRIPTION

The drawings will be first described.
Drawings

Figure 1:
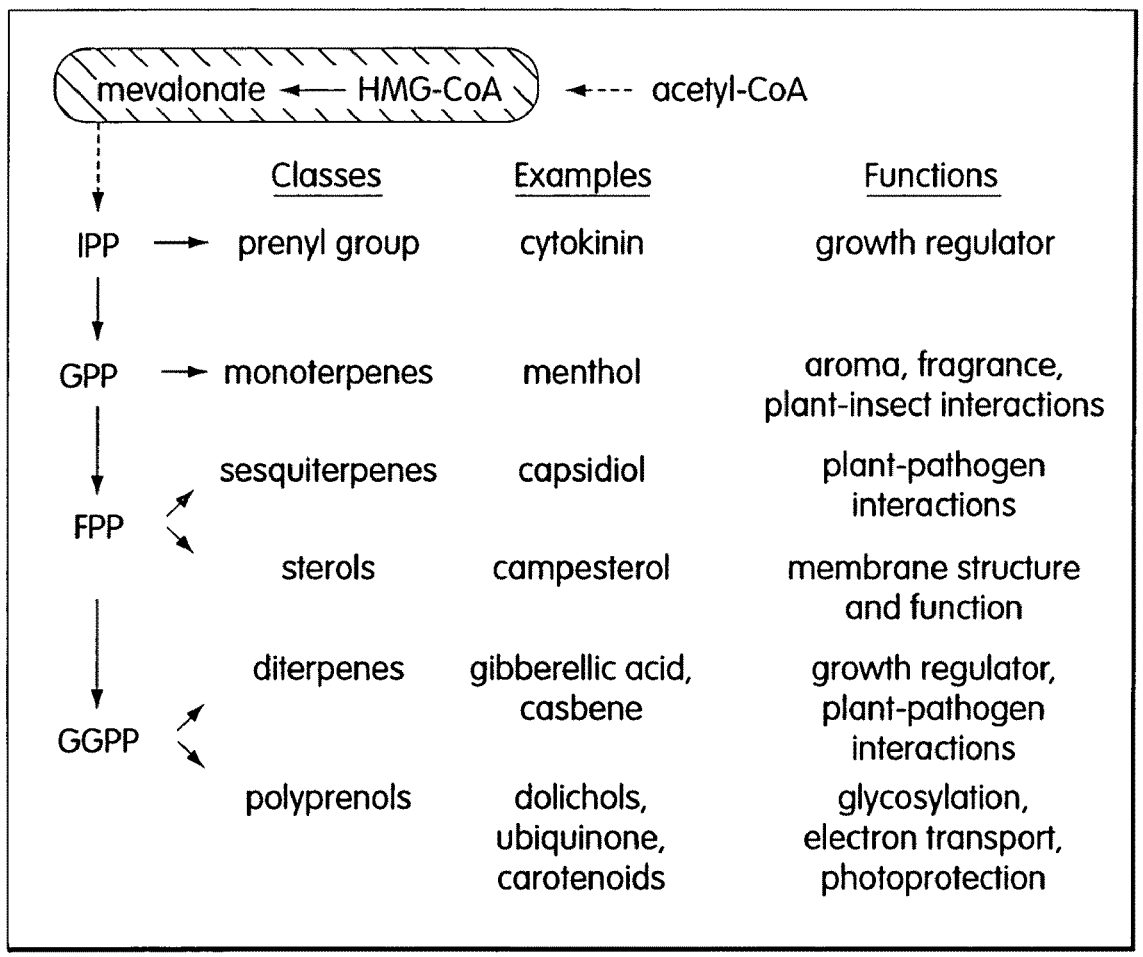
FIG. 1 is a schematic illustration showing the isoprenoid biosynthetic pathway with respect to the type of end products and their respective physiological functions. Broken arrows indicate multiple steps or reactions.
Figure 2:
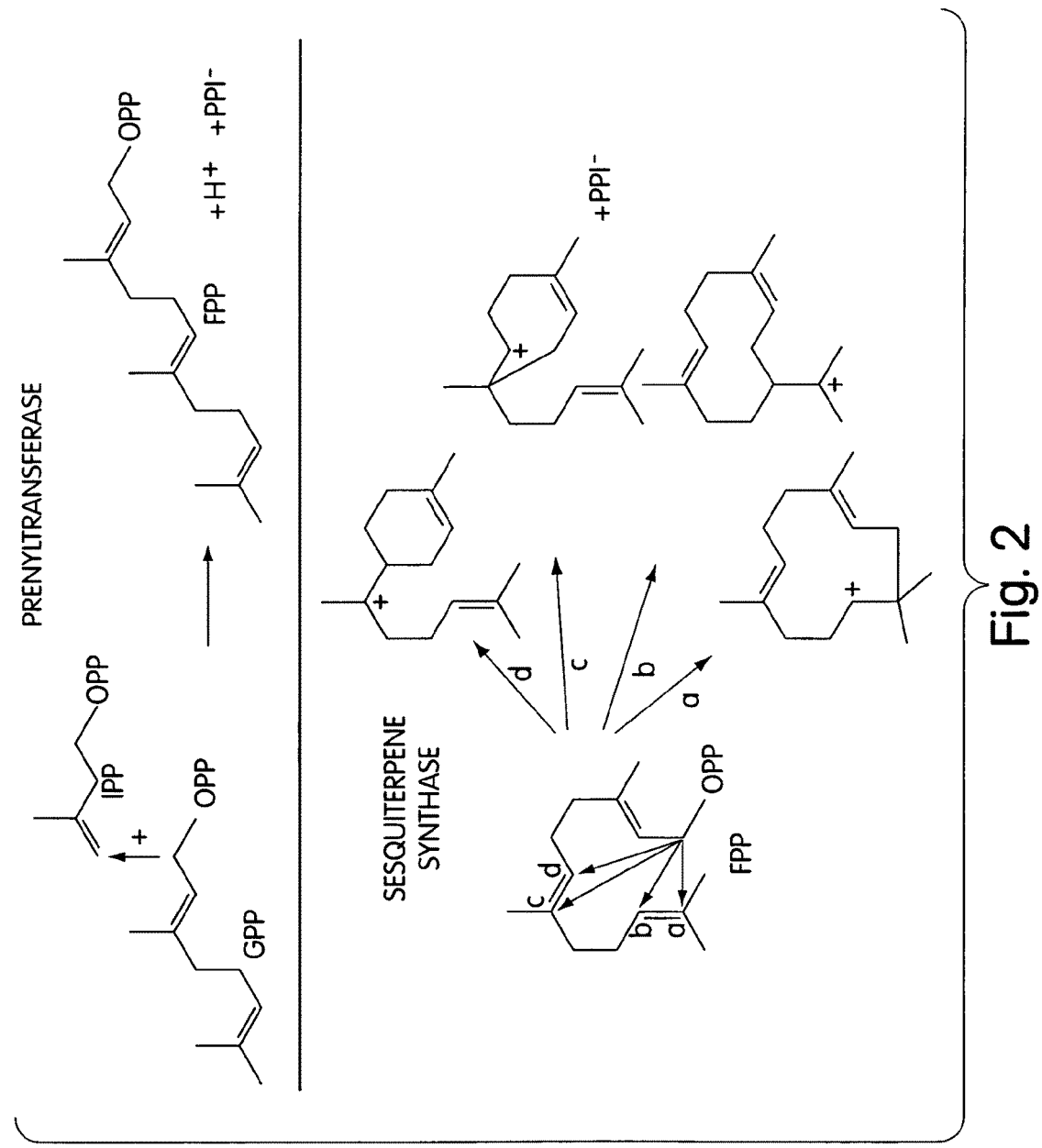
FIG. 2 is a schematic illustration showing the various reactions that are catalyzed by prenyltransferases and terpene synthases.
Figure 3:
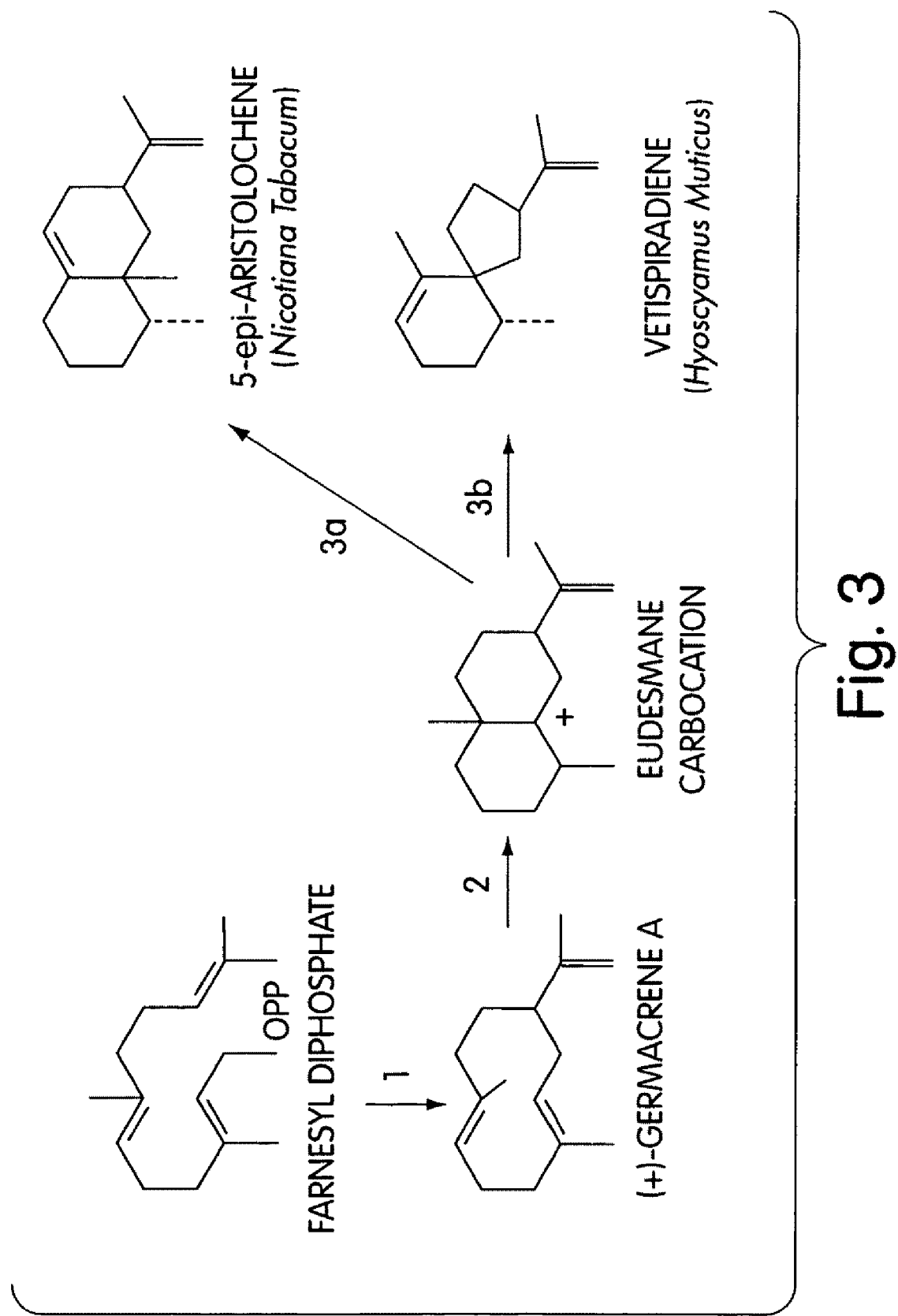

FIG. 3 is a schematic illustration showing a reaction mechanism for the synthesis of eremophilane (tobacco 5-epi-aristolochene synthase, TEAS) and vetispiradiene (*Hyoscyamus* vetispiradiene synthase, HVS) type sesquiterpene synthases. Partial reactions 1 and 2 are considered common to both types of synthases. Mechanistic differences in partial reactions 3a and 3b are sufficient to account for the different reaction products shown.

FIG. 4A is a schematic illustration showing the chimeric constructs used to map catalytic domains within sesquiterpene synthases. Line drawings depict composite diagrams for wildtype (i.e., TEAS and HVS) and chimeric (CH1-CH14) sesquiterpene synthase genes that were engineered into the bacterial expression vector pGBT-T19. Gene constructs were prepared using a combination of the available restriction endonuclease sites and amplification of select regions using PCR and PCR primers harboring convenient restriction endonuclease sites. Correspondence between unique restriction endonuclease sites and amino acid positions are noted.

Figure 4B:
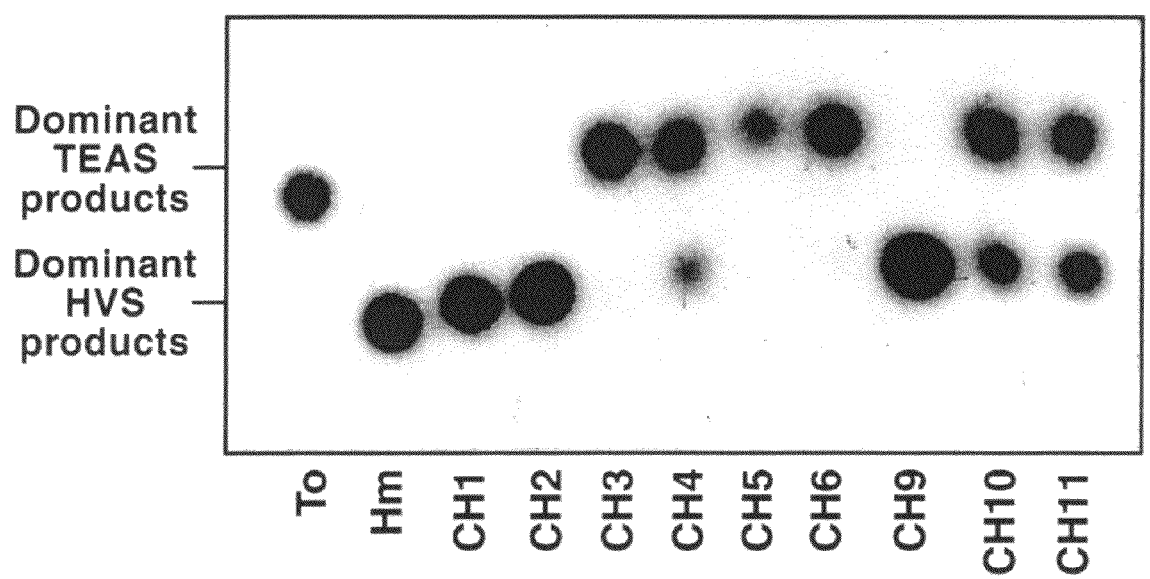

FIG. 4B is a photograph of a TLC experiment showing synthase enzyme activities in sonicated lysates of *E. coli* TB1 cells expressing the TEAS, HVS, and chimeric synthase constructs (CH1-CH14) and measured using .sup.3H-FPP. Reaction products were separated by argentation-TLC and detected by autoradiography. The radioactivity in 0.5 mm segments of each lane of an argentation-TLC plate was determined in a scintillation counter, and radioactivity associated with the zones for the TEAS and HVS specific products was set to 100%.

Figure 5:
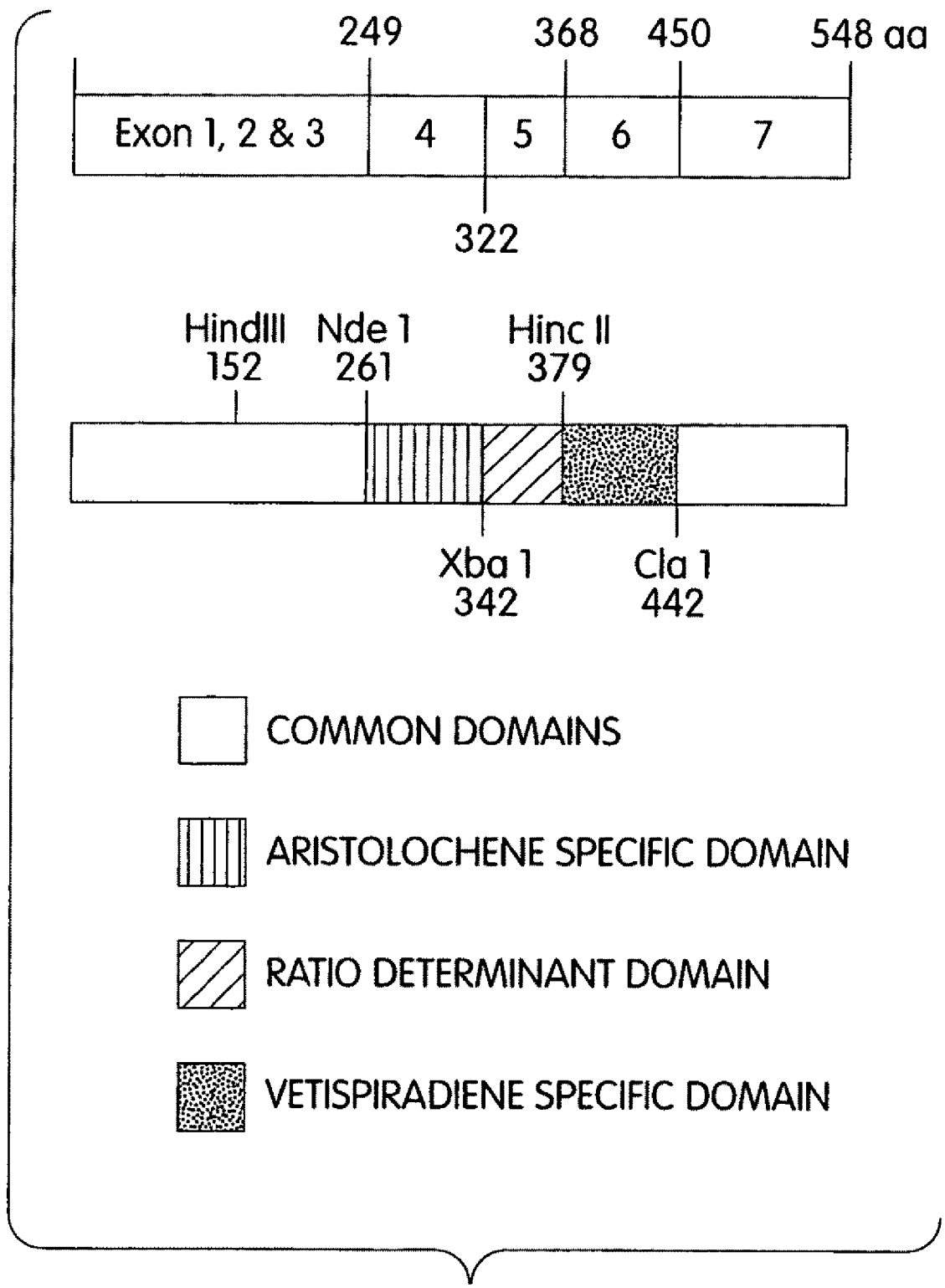

FIG. 5 is a schematic illustration showing the correspondence between exons and functional domains within isoprenoid synthases. The upper diagram represents the organization of exons within the TEAS gene, which is nearly identical to that of the HVS and casbene synthase genes. The lower diagram shows the alignment of functional domains to the exonic organization of the TEAS and HVS genes. Exon numbers are shown within the upper diagram, and all other numbers refer to amino acid positions, some of which correspond to the noted restriction endonuclease sites.

Figure 6:
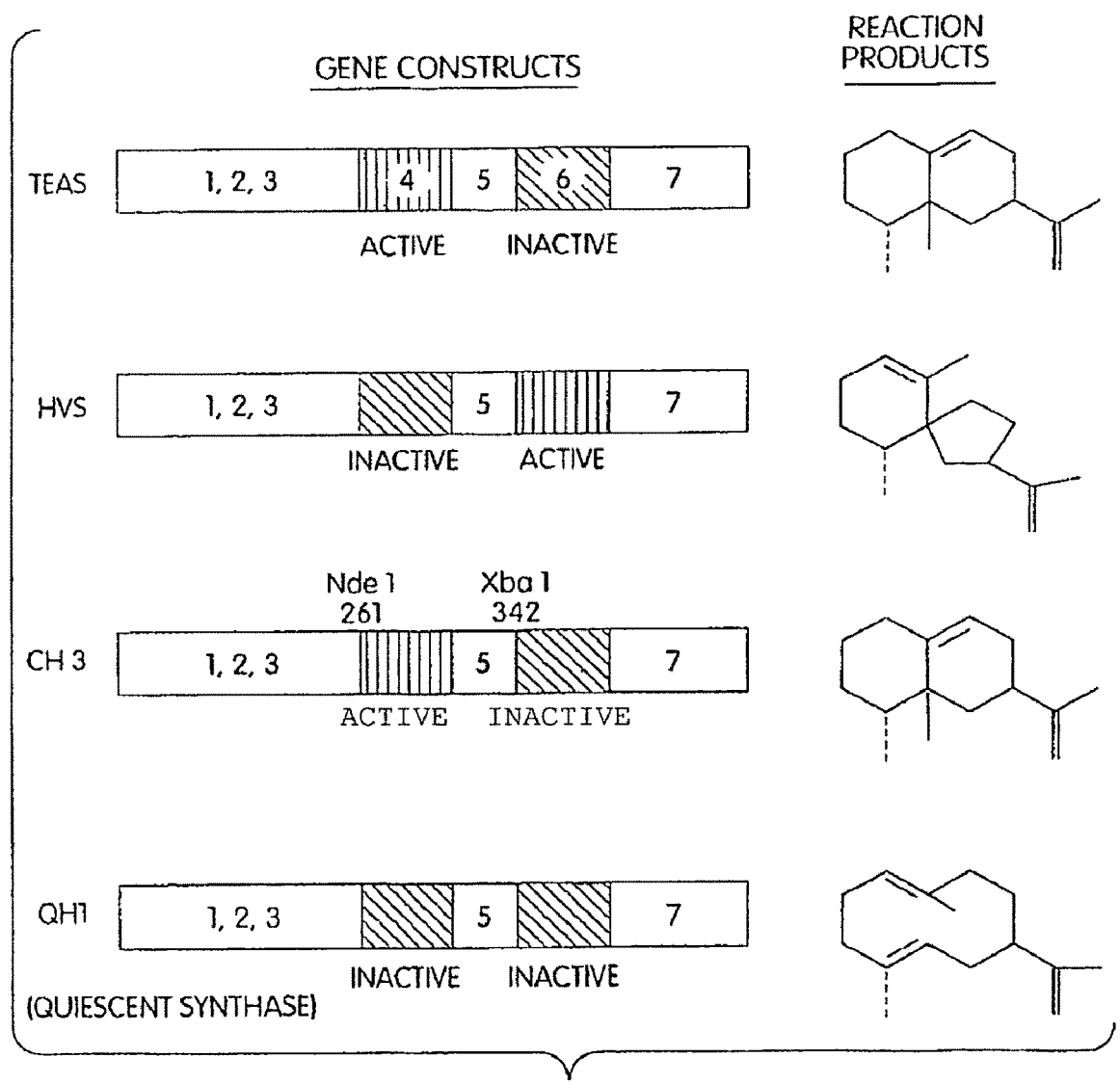

FIG. 6 is a schematic diagram showing a domain switching strategy used to generate a quiescent synthase (QH1). Substituting the inactive HVS domain corresponding to exon 4 into CH3 results in a synthase having an altered enzyme activity.

Figure 7:
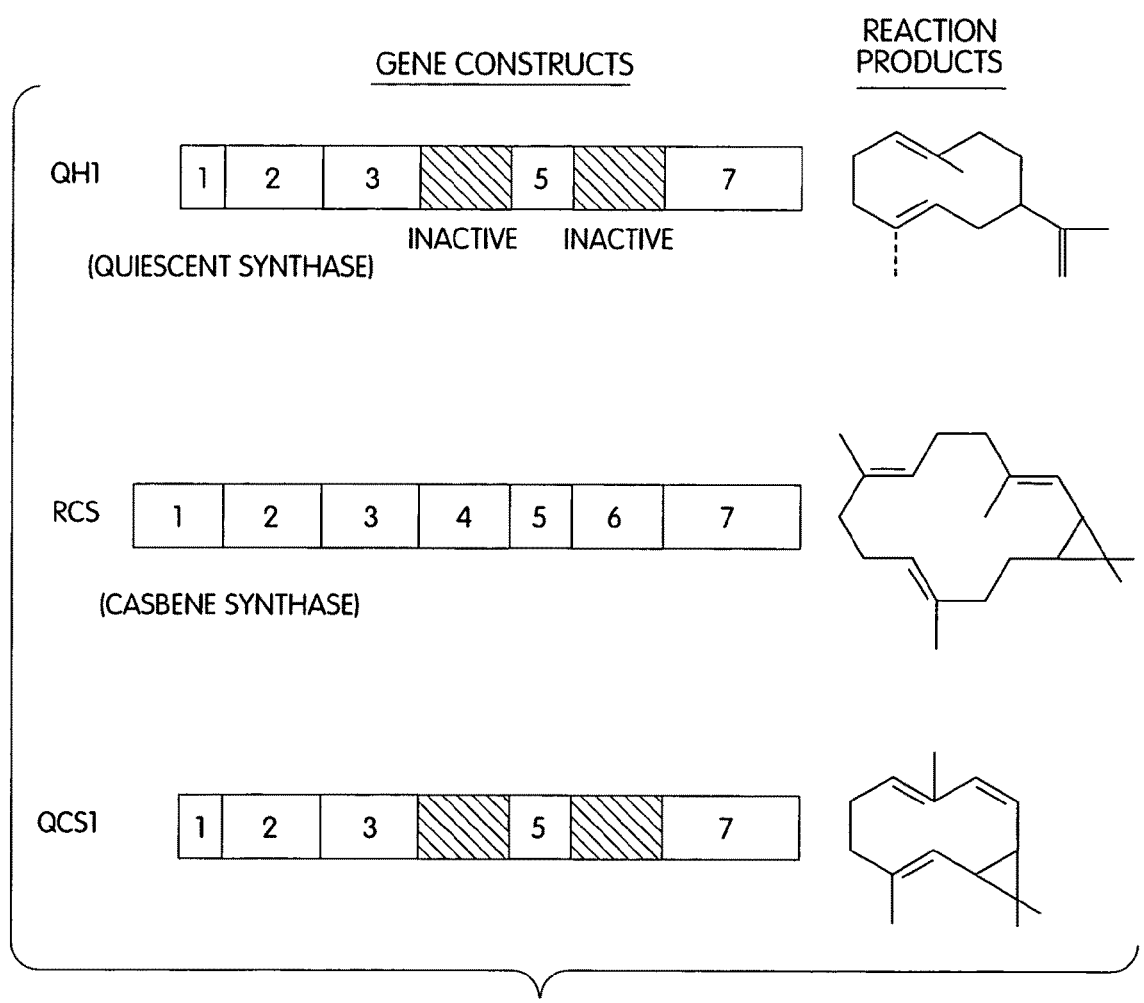

FIG. 7 is a schematic diagram of a domain switching strategy used for producing a chimeric quiescent-casbene synthase, and possible reaction products.

Figure 8:
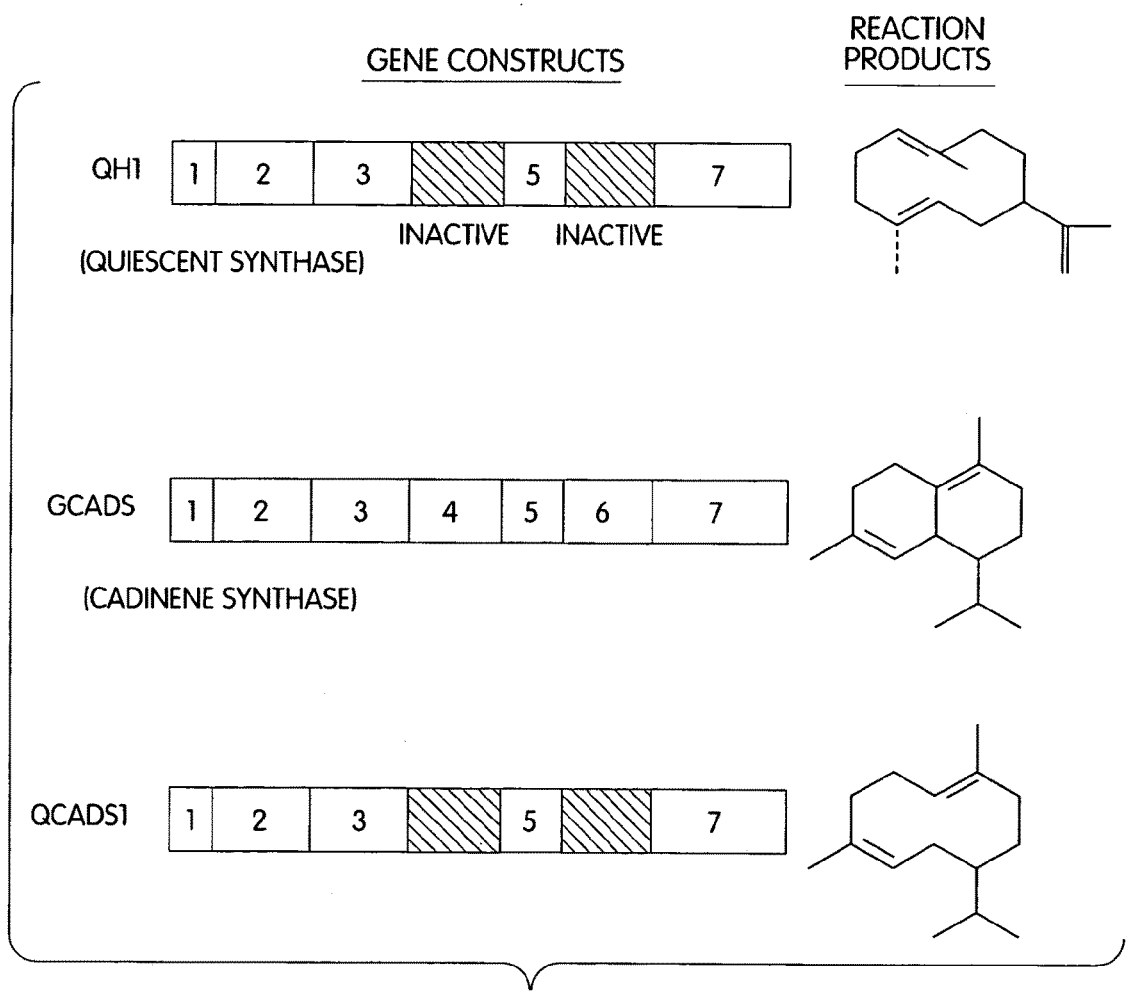

FIG. 8 is a schematic illustration of a domain switching strategy for producing a chimeric quiescent-cadinene synthase, and possible reaction products.

CHIMERIC ISOPRENOID SYNTHASES

Plasmids designed for expressing a chimeric synthase were generated by substituting a portion of a gene encoding a domain from tobacco 5-epi-aristolochene synthase with a portion of a gene encoding a domain from *Hyoscyamus* vetispiradiene synthase. These plasmids were expressed in bacteria, and bacterial lysates were prepared and assayed for sesquiterpene synthase activity. The sesquiterpene synthase assays included an argentation-thin layer chromatography (TLC) analysis which distinguished the aristocholene and vetispiradiene reaction products (Back and Chappell, *J. Biol. Chem.* 270:7375, 1995). As shown in FIG. 4A, fourteen chimeric synthase constructs were generated and were assayed as follows.

Full-length cDNAs for the tobacco 5-epi-aristolochene synthase (TEAS) and *Hyoscyamus* vetispiradiene synthase (HVS) were cloned into the EcoRI/XhoI sites of pBluescript SK (Stratagene), creating the pBSK-TEAS and pBSK-HVS plasmids, respectively (Back and Chappell, J Biol. Chem. 270:7375, 1995). The TEAS and HVS cDNA inserts of these expression plasmids were oriented with their translation start codons neighboring the EcoRI restriction site and their 3' poly A tail flanked by the XhoI restriction site of the pSK plasmid.

Chimeric synthases CH1, CH2, CH5, and CH7 were constructed by utilizing the conserved HindIII and NdeI restriction sites found between the tobacco and *Hyoscyamus* genes. CH1 was prepared by ligating the 5' terminal portion of the TEAS gene (corresponding to the EcoRI to HindIII fragment) with the 3' terminal portion of HVS gene (corresponding to the HindIII to KpnI fragment) into the bacterial expression vector pGBT-T19 (Gold Biotechnology) predigested with EcoRI and KpnI.

CH2 was prepared by ligating the 5' terminal portion of the TEAS gene (corresponding to the EcoRI to NdeI fragment) with the 3' terminal portion of HVS gene (corresponding to the NdeI to KpnI fragment) into pGBT-T19.

CH5 was prepared by ligating the 5' terminal portion of the HVS gene (corresponding to the EcoRI to HindIII fragment) with the 3' terminal portion of TEAS gene (corresponding to the HindIII to KpnI fragment) into pGBT-T19.

CH7 was prepared by ligating the 5' terminal portion of the HVS gene (corresponding to the EcoRI to NdeI fragment) with the 3' terminal portion of TEAS gene (corresponding to the NdeI to KpnI fragment) into pGBT-T19.

CH3, CH4, CH12, and CH13 were constructed using conventional polymerase chain reaction (PCR) methodologies, with primers designed for the amplification of particular segments of the HVS gene. To facilitate directional cloning and maintenance of reading frame, primers were also designed to contain convenient restriction sites.

CH3 was constructed as follows. An EcoRI/ClaI restriction fragment of the TEAS gene was isolated and ligated to the ClaI/KpnI fragment of the HVS gene. The HVS ClaI/KpnI fragment was prepared by PCR methodology using 5'-d (GGGATCGATGACATAGCCACGTATGAGGTT)-3' (SEQ ID NO: 1; ClaI restriction site underlined) as the forward primer and 5'-d (AATACGACTCACTATAG)-3' (SEQ ID NO: 2) as the reverse primer (corresponding to the T7 sequence found in the multiple cloning site of pBSK) using pBSK-HVS as the DNA template. The resulting restriction fragment was ligated into the EcoRI/KpnI sites of the pGBT-T19 vector.

CH4 and CH13 were constructed in a similar manner, but using the forward amplification primers 5'-d(CGA GTCAACATGGTTTATTGAGGGATA)-3' (SEQ ID NO: 3; HincII restriction site underlined) and 5'-d(TAT TCTAGATCTCTATGACGATTATGAA)-3' (SEQ ID NO: 4; XbaI restriction site underlined), respectively.

CH12 was prepared by ligating a PCR fragment corresponding to the first 1326 nucleotides of CH4 with the ClaI/KpnI fragment of the TEAS gene into the EcoRI/KpnI sites of the pGBT-T19 vector. The CH4 fragment was prepared using forward amplification primer 5'-d(GGGAGCTC GAATTCCATGGCCTCAGCAGCAGTTGCAAACTAT)-3' (SEQ ID NO: 5; EcoRI restriction site underlined and translation start codon in bold) and reverse primer 5'-d(GGG ATCGATAACTCTGCATAATGTAGCATT)-3' (SEQ ID NO: 6; ClaI restriction site underlined).

Chimeric synthases CH6, CH8, CH9, CH10, CH11, and CH14 were constructed as follows. Ligation of the EcoRI/HindIII fragment of the HVS gene with the HindIII/KpnI fragment of CH3 generated CH6. CH8 was created by ligating the EcoRI/NdeI fragment of HVS with the NdeI/KpnI fragment of CH3. CH9 was created by ligating the EcoRI/NdeI fragment of CH5 with the NdeI/KpnI fragment of HVS. CH10 was constructed by ligating the EcoRI/HindIII fragment of HVS with the HindIII/KpnI fragment of CH4. CH11 was constructed by ligating the EcoRI/NdeI fragment of HVS with the NdeI/KpnI fragment of CH4. And CH14 was generated by substituting the EcoRI/NdeI fragment of CH13 with the corresponding DNA fragment of pBSK-HVS. The nucleotide junctions of the chimeric constructs were confirmed by double-stranded DNA sequencing using the dideoxy nucleotide chain termination kit, according to the manufacturer's instructions (U.S. Biochemical Corp).

Chimeric synthases were expressed in *E. coli* TB1 cells. Procedures for growth of the bacterial cells, induction of gene expression, measurement of sesquiterpene synthase enzyme activity, and the determination of total protein in the bacterial lysates were performed according to the methods described by Back and Chappell (*Arch. Biochem. Biophys.* 315:527, 1994; *J. Biol. Chem.* 270:7375, 1995). Reaction products were separated by developing G60 silica TLC plates impregnated with 15% silver nitrate in benzene:hexane:diethyl ether (50:50:1). For qualitative evaluations, TLC plates were sprayed with Enhance surface fluorography spray (Dupont) and exposed to Kodak XAR-5 film for 2 to 5 days at −70° C. For quantitative evaluations, 0.5 mm zones of an entire lane from a TLC plates were scraped into scintillation vials, and the radioactivity was determined using a Packard 1500 Liquid Scintillation Counter. The dominant reaction products generated by the synthase activities resulting from expression of the TEAS, HVS, CH4, and CH14 constructs in bacterial lysates were also verified by gas chromatography (GC) and gas chromatography-mass spectroscopy (GC-MS) according to the conditions described by Chappell et al. (*Phytochemistry* 26:2259, 1987) (data not shown). In addition, mass spectra profiles were compared to that published for 5-epi-aristolochene (Anke and Sterner, *Planta Med.* 57:344, 1991) and the predicted fragmentation pattern for vetispiradiene (Enzell et al., *Mass Spectrometry Rev.* 3:395, 1984).

As shown in FIGS. 4A-B, the dominant reaction product resulting from the expression of the tobacco TEAS gene expressed was 5-epi-aristolochene, and vetispiradiene was found to be the dominant reaction product resulting from the expression of the HVS gene. The predominant reaction products generated by the expression of CH1 and CH2 were also HVS-specific (i.e., vetispiradiene), with enzyme specific activities similar to those found for HVS that was expressed from the pBSK-HVS plasmid. These results indicated that the amino-terminal half of TEAS and HVS were functionally equivalent with respect to the HVS carboxy-terminus and do not contribute to the specificity of the reaction product. CH7, having an HVS amino terminus and a TEAS carboxy terminus, is the converse construct of CH2, and the resulting synthase activity was expected to result in expression of a TEAS-specific product (i.e., 5-epi-aristolochene). Immunodetection assays revealed that synthase protein produced upon expression of CH7 was found to be of the correct size and expected abundance (data not shown); however, no enzyme activity was detected. The lack of enzyme activity indicated that interactions between the carboxy and amino terminal portions of the protein contributed to enzyme activity. This interpretation is further supported by comparing the specific activity of the enzymes generated by the expression of the CH5 and CH6 constructs. CH5 resulted in the expression of a product having a 10-fold lower specific activity of synthase enzyme activity than the other chimeric synthases, even though the absolute level of expressed protein was similar to the other constructs (as determined by immunodetection, data not shown). Substituting an HVS carboxy-terminal region was found to restore the specific activity to the synthase enzyme that was generated by CH6.

Comparison of CH2 and CH3 chimeric synthases provided evidence for specificity of end-product formation residing within a domain of approximately 181 amino acids, corresponding to the NdeI and ClaI restriction sites within the TEAS and HVS genes. Expression of CH4 unexpectedly resulted in the production of a chimeric synthase protein capable of generating reaction products reflective of both the TEAS and HVS enzymes. We interpreted this result to indicate that amino acids 261 to 379 within the tobacco 5-epi-aristolochene synthase are responsible for the TEAS-specific products (i.e., the region corresponding to the NdeI to HindIII fragment of the cDNA), while amino acids 379 to 442 within the *Hyoscyamus* protein are responsible for the HVS-specific products (i.e., the region corresponding to the HincII to ClaI fragment of the cDNA).

Our interpretation was confirmed by evaluating the expression products of CH11 and CH12. CH11 represented the substitution of the NdeI to Hindi fragment of the *Hyoscyamus* gene with the corresponding tobacco gene fragment, and resulted in the production of an enzyme having HVS- and TEAS-specificity. CH12 represented a substitution of the Hindi to ClaI fragment of the tobacco gene with the corresponding *Hyoscyamus* gene fragment, and resulted in the production of an enzyme having HVS- and TEAS-specificity. Comparing CH11 to CH13 provided a further refinement in the domain characterization of the tobacco enzyme responsible for the TEAS-specific products. The fact that CH13 was found to be a multifunctional enzyme indicated that the 81 amino acids encoded by the DNA fragment residing between the NdeI to XbaI restriction sites of the tobacco cDNA were sufficient for formation of the predominant TEAS specific products. This interpretation was confirmed by substituting the domain contained within the NdeI/XbaI HVS cDNA restriction fragment of CH14 with that of the TEAS gene (FIG. 4A).

As shown in FIG. 4B, the predominant reaction product(s) of the wildtype tobacco TEAS and *Hyoscyamus* HVS genes expressed in bacteria migrated on silver nitrate-TLC plates with $R_f$ values of 0.41 and 0.31, values consistent with previous characterization of these products as 5-epi-aristolochene and vetispiradiene, respectively (Back and Chappell, *J Biol. Chem.* 270:7375, 1995; Back et al., *Arch. Biochem. Biophys.* 315:527, 1994). GC and GC-MS analyses indicated that the predominant TEAS reaction products were 5-epi-aristolochene (70% of total products, based on percentage of total peak areas from GC analysis) and a bicyclic sesquiterpene (20%) ([M]$^+$ ion at m/z of 204). The predominant HVS reaction product was vetispiradiene (>90%) ([M]$^+$ ion at m/z of 204 with a base peak at m/z 41 and a series of predictable ions at m/z 175, 108, 94, and 68), and the predominant reaction products of CH4 were 5-epi-aristolochene (18%), a bicyclic sesquiterpene (43%), and vetispiradiene (32%) (data not shown).

In addition, studies relying on affinity purification of histidine-tagged recombinant synthase proteins has revealed five other minor reaction products, each representing approximately 1% of the total products, with all five found at the same relative abundance in all the reaction assays.

Ratio-Determinant Domain

Another domain of the synthase proteins was identified by comparing the relative ratio of the predominant reaction products produced by the multifunctional chimeric synthase enzymes (FIG. 4A). For example, the reaction products resulting from expression of constructs CH4, CH10, CH11, and CH12 were generated in a ratio of 60-70% TEAS-specific to 30-40% HVS-specific. In contrast, an inverse ratio of reaction products resulted from expression of constructs CH13 and CH14. This result indicated that the region encompassed by the XbaI to HincII domain influenced the relative ratio of reaction products generated by the multifunctional chimeric synthase enzymes. These results indicated that two separate and distinct domains within the synthase peptide contributed directly to the types of reaction products generated, and are interrupted by another domain which we refer to as the ratio-determinant domain (FIG. 5).

Site-Directed Mutagenesis

Additional analysis of the product specificity and ratio determinant domains was determined using conventional site-directed mutagenesis methodologies. The results of this analysis are presented in Table I (below). For example, the DDXXD motif, found within the aristolochene specific domain, is a conserved sequence that is found in a variety of terpene biosynthetic enzymes including TEAS and HVS. This acidic amino acid cluster is said to coordinate a metal cofactor that is necessary to neutralize the diphosphate moiety of FPP in an otherwise lipophilic pocket. Substitution of the first aspartic acid residue (D301) of the DDXXD motif with either glutamic acid (overall charge conservation) or valine (net loss of acidic charge) residues (i.e., D301→E and D301→V) resulted in the formation of an inactivated enzyme. A conserved substitution of the second aspartic acid (D302) with a glutamic acid residue (i.e., D302→E) also inactivated chimeric synthase enzyme activity by 95%, and resulted in a slight alteration of the product distribution of the multifunctional enzyme.

TABLE I

| Mutation target gene | Mutated amino acid | Product ratio | | Specific Activity (nmol/mg h$^{-1}$) |
|---|---|---|---|---|
| | | Aristolochene | Vetispiradiene | |
| CH4 | | 66% | 34% | 34 |
| Substrate binding domain (NdeI/XbaI region) | | | | |
| Tobacco CH4 | D301V | No activity | | 0 |
| CH4 | R287A | No activity | | 0 |
| CH4 | D301V | No activity | | 0 |
| CH4 | D301E | No activity | | 0 |
| CH4 | D302E | 51% | 49% | 1.8 |
| Ratio determinant domain (XbaI/HincII region) | | | | |
| CH4 | K347I | 64% | 36% | 32 |
| CH4 | H360S | 63% | 32% | 29 |
| CH4 | H364S | 65% | 35% | 38 |
| Hyoscyamus specific domain (HincII/ClaI region) | | | | |
| CH4 | T408A | 67% | 33% | 48 |
| CH4 | K420M | 68% | 32% | 29 |
| CH4 | H422A | 67% | 33% | 30 |
| CH4 | N436S | 70% | 30% | 32 |
| CH4 | AT437, 438VI | 61% | 39% | 33 |

The sites for directed substitutions within the ratio-determinant domain (i.e., K347→I, H360→S, H364→S) were inferred by an analysis of reports that hypothesized the importance of charged amino acid residues (e.g., histidine or lysine) in synthase enzymology, and these sites represented those amino acids which displayed the greatest charge differences in comparisons between the TEAS and HVS primary sequences. None of the three mutations analyzed had any effect on overall catalytic activity or the ratio of products formed.

Amino acid substitutions within the HVS specific domain were chosen on the basis of comparisons between secondary structural predictions of the HVS and TEAS proteins. Those amino acids mutated appeared to contribute disproportionately to structural distortions in the secondary structure models of these two proteins, largely because of charge considerations. However, as shown in Table I (above), substitutions involving charged to non-charged (i.e., T408→A, K420→M, H422→A) or reduced charged (N436→S, A437→T, V438→I) amino acids did not affect overall enzyme activity, nor the synthesis rate of one product or the other.

Quiescent Synthases

To generate a quiescent synthase, the inactive domain corresponding to exon 4 of HVS is substituted with the corresponding active domain of CH3, as outlined in FIG. 6. CH3 contains an inactive domain corresponding to exon 6 of TEAS, has convenient NdeI and XbaI restriction sites for the desired substitution, and can be overexpressed in bacteria to high levels. Domain switching is accomplished using standard molecular techniques, as described herein. In one particular example, a PCR amplification product of HVS cDNA corresponding to exon 4, encompassing amino acids 261 to 342 and containing appropriate NdeI and XbaI sites within the primers, is substituted for the corresponding region of CH3. In generating such constructs, care is exercised to maintain appropriate amino acid residues and the correct reading frame, and expression testing of the construct entails a measurement of the protein level in the soluble and insoluble fractions of bacterial lysates by immunoblotting techniques, as well as by enzyme assays.

In addition, large scale enzyme reactions are performed, the reaction product(s) are extracted into hexane, and the products are purified by HPLC methods. Additional evaluation of the quiescent enzyme reaction products is carried out using TLC, and comparing the $R_f$ values of the experimental sample to those generated by the TEAS and HVS enzymes. Retention times of the reaction products (e.g., germacrene or germacrene-like reaction product) are also monitored using GC, GC-MS, and NMR according to standard methods.

The quiescent synthase is useful for providing sufficient amounts of the germacrene reaction intermediate(s) (or derivatives thereof) to confirming the chemical rationalization for the EAS and VS reactions, and produces a template chimeric synthase that may be used for the introduction of novel terminal steps in the overall synthase reaction scheme.

Chimeric Casbene and Cadinene Synthases

Chimeric isoprenoid synthases are also useful for generating novel macrocyclic isoprenoids or isoprenoids having altered stereochemical properties. For example, isoprenoid synthases such as casbene synthase, a diterpene synthase which catalyzes the synthesis of a macrocyclic diterpene harboring a cyclopropyl side group, and cadiene synthase, a sesquiterpene synthase that catalyzes the synthesis of a bicyclic sesquiterpene, provide domains useful for engineering enzymes capable of producing macrocyclic isoprenoids or isoprenoid reaction products having altered sterochemical properties. A general scheme for producing such chimeric synthases is presented in FIGS. 7 and 8.

To construct such chimeric casbene and cadienne synthases, quiescent amino terminal domains (and other synthase domains, as necessary) are substituted with those from casbene and cadinene synthase using convenient restriction sites and PCR amplification of selected regions as described above. Sequences corresponding to the N-terminal, plastid targeting sequence of the casbene synthase are deleted in these constructs. Chimeric constructs are expressed in bacteria, bacterial lysates are examined for chimeric synthase activity, and reaction products are characterized as described above, for example, using argentation-TLC. Constructs supporting high levels of synthase activity in bacteria and/or activity generating reaction products which migrate with Rfs different from aristolochene and vetispiradiene standards are considered useful in the invention. Reaction products are also analyzed for their retention times by GC and subjected to GC-MS and NMR, as necessary. Those domains of casbene synthase and cadinene synthase which contribute to the synthesis of unique reaction products may also be subjected to fine detail mapping using a strategy analogous to that depicted in FIG. 4A.

Production of Other Chimeric Isoprenoid Synthases

Using the standard molecular techniques described herein, other chimeric synthases may be readily generated which include domains from known or newly isolated synthase enzymes. Such chimeric synthases may be tested for activity using, for example, any appropriate enzyme assays known to those in the art, or by standard immunodetection techniques.

The isolation of additional synthase coding sequences is also possible using standard cloning strategies and techniques that are well known in the art. For example, using all or a portion of the amino acid sequence of a known synthase polypeptide, one may readily design synthase-specific oligonucleotide probes, including synthase degenerate oligonucleotide probes (i.e., a mixture of all possible coding sequences for a given amino acid sequence). These oligonucleotides may be based upon the sequence of either DNA strand and any appropriate portion of synthase nucleotide sequence. General methods for designing and preparing such probes are provided, for example, in Ausubel et al., 1996, *Current Protocols in Molecular Biology*, Wiley Interscience, New York, and Berger and Kimmel, *Guide to Molecular Cloning Techniques*, 1987, Academic Press, New York. These oligonucleotides are useful for synthase gene isolation, either through their use as probes capable of hybridizing to a synthase complementary sequences or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); Chen at al. *Arch. Biochem. Biophys.* 324:255, 1995; and Sambrook et al., *Molecular Cloning: A Laboratory Manual*, Cold Spring Harbor Laboratory Press, New York. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

As discussed above, synthase oligonucleotides may also be used as primers in amplification cloning strategies, for example, using PCR. PCR methods are well known in the art and are described, for example, in PCR Technology, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, a synthase gene may be isolated using the PCR "RACE" technique, or Rapid Amplification of cDNA Ends (see, e.g., Innis et al. (supra)). By this method, oligonucleotide primers based on a synthase sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, (1988).

Useful synthase sequences may be isolated from any appropriate organism. Confirmation of a sequence's relatedness to the synthase polypeptide family may be accomplished by a variety of conventional methods, for example, sequence comparison. In addition, the activity of any synthase protein may be evaluated according to any of the techniques described herein.

Chimeric Isoprenoid Synthase Polypeptide Expression

Chimeric synthase polypeptides may be produced by transformation of a suitable host cell with all or part of a chimeric synthase DNA (for example, the chimeric synthase cDNAs described above) in a suitable expression vehicle or with a plasmid construct engineered for increasing the expression of a chimeric synthase polypeptide in vivo.

Those skilled in the field of molecular biology will appreciate that any of a wide variety of expression systems may be used to provide the recombinant protein. The precise host cell used is not critical to the invention. The chimeric synthase protein may be produced in a prokaryotic host, for example, *E. coli* TB1, or in a eukaryotic host, for example, *Saccharomyces cerevisiae*, mammalian cells (for example, COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include, but are not limited to, Conifers, Petunia, Tomato, Potato, Tobacco, *Arabidopsis*, Lettuce, Sunflower, Oilseed rape, Flax, Cotton, Sugarbeet, Celery, Soybean, Alfalfa, *Medicago*, Lotus, *Vigna*, Cucumber, Carrot, Eggplant, Cauliflower, Horseradish, Morning Glory, Poplar, Walnut, Apple, Asparagus, Rice, Maize, Millet, Onion, Barley, Orchard grass, Oat, Rye, and Wheat.

Such cells are available from a wide range of sources including: the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; and Gasser and Fraley, *Science* 244:1293, (1989).

For prokaryotic expression, DNA encoding a chimeric synthase polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac), the tryptophan (Trp) (Goeddel et al., *Nucl. Acids Res.* 8:4057 (1980)), and the tac promoter systems, as well as the lambda-derived $P_L$ promoter and N-gene ribosome binding site (Simatake et al., *Nature* 292:128 (1981)).

One particular bacterial expression system for chimeric synthase polypeptide production is the *E. coli* pET expression system (Novagen). According to this expression system, DNA encoding a chimeric synthase polypeptide is inserted into a pET vector in an orientation designed to allow expression. Since the chimeric synthase gene is under the control of the T7 regulatory signals, expression of chimeric synthase is induced by inducing the expression of T7 RNA polymerase in the host cell. This is typically achieved using host strains which express T7 RNA polymerase in response to IPTG induction. Once produced, recombinant chimeric synthase polypeptide is then isolated according to standard methods known in the art, for example, those described herein.

Another bacterial expression system for chimeric synthase polypeptide production is the pGEX expression system (Pharmacia). This system employs a GST gene fusion system that is designed for high-level expression of a gene or gene fragment as a fusion protein with rapid purification and recovery of the functional gene product. The chimeric synthase protein of interest is fused to the carboxyl terminus of the glutathione S-transferase protein from Schistosoma japonicum and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

For eukaryotic expression, the method of transformation or transfection and the choice of vehicle for expression of the chimeric synthase polypeptide will depend on the host system selected. Transformation and transfection methods of numerous organisms, for example, the baker's yeast Saccharomyces cerevisiae, are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., *Proc. Natl. Acad. Sci. U.S.A* 87:1228 (1990); Potrykus, I., *Annu. Rev. Plant Physiol. Plant Mol. Biology.* 42:205 (1991); and BioRad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred eukaryotic expression system is the mouse 3T3 fibroblast host cell transfected with a pMAMneo expression vector (Clontech). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a chimeric synthase polypeptide is inserted into the pMAMneo vector in an orientation designed to allow expression. The recombinant chimeric synthase polypeptide is then isolated as described below. Other preferable host cells which may be used in conjunction with the pMAMneo expression vehicle include COS cells and CHO cells (ATCC Accession Nos. CRL 1650 and CCL 61, respectively).

Alternatively, if desired, a chimeric synthase polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the chimeric synthase polypeptide is cloned into an expression vector which includes the dihydrofolate reductase (DHFR) gene. Integration of the plasmid and, therefore, the chimeric synthase-encoding gene into the host cell chromosome is selected for by inclusion of 0.01-300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHrF and pAdD26SV(A) (described in Ausubel et al., supra). Any of the host cells described above or, preferably, a DHFR-deficient CHO cell line (for example, CHO DHFR-cells, ATCC Accession No. CRL 9096) are among the host cells preferred for DHFR selection of a stably-transfected cell line or DHFR-mediated gene amplification.

A chimeric synthase polypeptide is preferably produced by a stably-transfected plant cell line or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned chimeric synthase gene under the transcriptional control of 5' and 3' regulatory sequences and (2) a dominant selectable marker. Such plant expression vectors may also contain, if desired, a promoter regulatory region (for example, one conferring inducible or constitutive expression, or environmentally- or developmentally-regulated, or pathogen- or wound-inducible, or cell- or tissue-specific expression), a transcription initiation start site, a ribosome binding site, an RNA processing signal, a transcription termination site, and/or a polyadenylation signal.

The chimeric synthase DNA sequence of the invention may, if desired, be combined with other DNA sequences in a variety of ways. The chimeric synthase DNA sequence of the invention may be employed with all or part of the gene sequences normally associated with a synthase protein. In its component parts, a DNA sequence encoding a chimeric synthase protein is combined in a DNA construct having a transcription initiation control region capable of promoting transcription and translation in a host cell.

In general, the constructs will involve regulatory regions functional in plants which provide for production of a chimeric synthase protein as discussed herein. The open reading frame coding for the chimeric synthase protein or functional fragment thereof will be joined at its 5' end to a transcription initiation regulatory region such as the sequence naturally found in the 5' upstream region of a synthase structural gene. Numerous other transcription initiation regions are available which provide for constitutive or inducible regulation.

For applications when developmental, cell, tissue, hormonal, environmental, or pathogen-inducible expression are desired, appropriate 5' upstream non-coding regions are obtained from other genes; for example, from genes regulated during seed development, embryo development, leaf development, or in response to a pathogen.

Regulatory transcript termination regions may also be provided in DNA constructs of this invention as well. Transcript termination regions may be provided by the DNA sequence encoding a synthase protein or any convenient transcription termination region derived from a different gene source. The transcript termination region will contain preferably at least 1-3 kb of sequence 3' to the structural gene from which the termination region is derived. Such genetically-engineered plants are useful for a variety of industrial and agricultural applications as discussed below. Importantly, this invention is applicable to gymnosperms and angiosperms, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313:810 (1985)). The CaMV promoter is also highly active in monocots (see, e.g., Dekeyser et al., Plant Cell 2:591 (1990); Terada and Shimamoto, *Mol. Gen. Genet.* 220:389, (1990)). Moreover, activity of this promoter can be further increased (i.e., between 2-10 fold) by duplication of the CaMV 35S promoter (see e.g., Kay et al., *Science* 236:1299 (1987); Ow et al., *Proc. Natl. Acad. Sci. U.S.A.* 84:4870 (1987); and Fang et al., *Plant Cell* 1:141 (1989)).

Other useful plant promoters include, without limitation, the nopaline synthase promoter (An et al., *Plant Physiol.* 88:547 (1988)) and the octopine synthase promoter (Fromm et al., *Plant Cell* 1:977 (1989)).

For certain applications, it may be desirable to produce the chimeric synthase gene product in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88:965 (1988); Takahashi and Komeda, *Mol. Gen. Genet.* 219:365 (1989); and Takahashi et al. *Plant J.* 2:751 (1992)), light-regulated gene expression (e.g., the pea rbcS-3A described by Kuhlemeier et al. (*Plant Cell* 1:471 (1989); the maize rbcS promoter described by Schaffner and Sheen, (*Plant Cell* 3:997 (1991); or the chlorophyll a/b-binding protein gene found in pea described by Simpson et al. (*EMBO J* 4:2723 (1985)), hormone-regulated gene expression (for example, the abscisic acid (ABA) responsive sequences from the Em gene of wheat described by Marcotte et al. (*Plant Cell* 1:969 (1989); the ABA-inducible HVA1 and HVA22, and the rd29A promoters described for barley and *Arabidopsis* by Straub et al. (*Plant Cell* 6:617 (1994), Shen et al. (*Plant Cell* 7:295 (1994)), and wound-induced gene expression (for example, of wunI described by Siebertz et al. (*Plant Cell* 1:961 (1989)), or organ-specific gene expression (for example, of the tuber-specific storage protein gene described by Roshal et al. (*EMBO J.* 6:1155 (1987); the 23-kDa zein gene from maize described by Schernthaner et al. (*EMBO J.* 7:1249 (1988); or the French bean 13-phaseolin gene described by Bustos et al. (*Plant Cell* 1:839 (1989)); and pathogen-inducible gene expression described by Chappell et al. in U.S. Ser. Nos. 08/471,983, 08/443,639, and 08/577,483, hereby incorporated by reference.

Plant expression vectors may also optionally include RNA processing signals, for example, introns, which have been shown to be important for efficient RNA synthesis and accumulation (Callis et al., *Genes and Dev.* 1:1183 (1987)). The location of the RNA splice sequences can dramatically influence the level of transgene expression in plants. In view of this fact, an intron may be positioned upstream or downstream of a chimeric synthase polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84:744 (1987); An et al., *Plant Cell* 1:115 (1989)). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Alternatively, the green-fluorescent protein from the jellyfish *Aequorea victoria* may be used as a selectable marker (Sheen et al., *Plant J.* 8:777, 1995; Chiu et al., *Current Biology* 6:325 (1996)). Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst A G, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75-100 µg/ml (kanamycin), 20-50 µg/ml (hygromycin), or 5-10 µg/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*) (see, e.g., Lichtenstein and Fuller In: *Genetic Engineering*, vol 6, P W J Rigby, ed, London, Academic Press, 1987; and Lichtenstein, C. P., and Draper, J, In: *DNA Cloning*, Vol II, D. M. Glover, ed, Oxford, IRI Press, 1985)), (2) the particle delivery system (see, e.g., Gordon-Kamm et al., *Plant Cell* 2:603 (1990); or BioRad Technical Bulletin 1687, supra), (3) microinjection protocols (see, e.g., Green et al., supra), (4) polyethylene glycol (PEG) procedures (see, e.g., Draper et al., *Plant Cell Physiol.* 23:451 (1982); or e.g., Zhang and Wu, *Theor. Appl. Genet.* 76:835 (1988)), (5) liposome-mediated DNA uptake (see, e.g., Freeman et al., *Plant Cell Physiol.* 25:1353 (1984)), (6) electroporation protocols (see, e.g., Gelvin et al., supra; Dekeyser et al., supra; Fromm et al., *Nature* 319:791 (1986); Sheen, *Plant Cell* 2:1027 (1990); or Jang and Sheen *Plant Cell* 6:1665 (1994)), and (7) the vortexing method (see, e.g., Kindle supra). The method of transformation is not critical to the present invention. Any method which provides for efficient transformation may be employed. As newer methods are available to transform crops or other host cells, they may be directly applied.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the present invention, the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plants cells transformed with plant expression vectors can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned chimeric synthase polypeptide under the control of the EAS4 promoter and the nopaline synthase terminator and carrying a selectable marker (for example, kanamycin resistance) is transformed into *Agrobacterium*. Transformation of leaf discs (for example, of tobacco leaf discs), with vector-containing *Agrobacterium* is carried out as described by Horsch et al. (*Science* 227:1229 (1985)). Putative transformants are selected after a few weeks (for example, 3 to 5 weeks) on plant tissue culture media containing kanamycin (e.g., 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly effect the levels and the tissue and developmental patterns of transgene expression. Consequently, a number of transgenic lines are usually screened for each transgene to identify and select plants with the most appropriate expression profiles.

Transgenic lines are generally evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies to the chimeric synthase (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant chimeric synthase protein is expressed in any cell or in a transgenic plant (for example, as described above), it may be isolated, e.g., using affinity chromatography. In one example, an anti-chimeric synthase antibody (e.g., produced as described in Ausubel et al., supra, or by any standard technique) may be attached to a column and used to isolate the polypeptide. Lysis and fractionation of chimeric synthase-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, *Laboratory Techniques In Biochemistry And Molecular Biology*, eds., Work and Burdon, Elsevier, 1980).

These general techniques of polypeptide expression and purification can also be used to produce and isolate useful chimeric synthase fragments or analogs.

Use

The invention described herein is useful for a variety of agricultural, pharmaceutical, industrial, and commercial purposes. For example, the methods, DNA constructs, proteins, and transgenic organisms, including the bacteria, yeast, and plants described herein, are useful for improving isoprenoid synthesis, manufacturing, and production.

Our results presented above demonstrate that it is possible to modulate isoprenoid synthase activity by providing chimeric synthases. In this manner, various synthase reaction products may be modified, controlled, or manipulated, resulting in enhancement of production of numerous synthase reaction products, for example, the production of novel monoterpenes, diterpenes, and sesquiterpenes. Such compounds are useful as phytoalexins, insecticides, perfumes, and pharmaceuticals such as anti-bacterial and fungal agents.

A number of chimeric isoprenoid synthases may be engineered that are useful, for example, for the production of compounds having anti-fungal, anti-bacterial, anti-malarial, and anti-tumor properties. For example, for the production of chimeric synthases capable of catalyzing the production of anti-fungal isoprenoids, the C-terminal domain of casbene synthase (Mau and West, *Proc. Natl. Acad. Sci.* 91:8497, 1994) is joined to the N-terminal domain of TEAS, HVS, or CH9. To produce a chimeric synthase capable of catalyzing the production of anti-bacterial compounds, the C-terminal domain of cyclofamesenone synthase (Habtermariam et al., *J. Nat. Prod.* 56:140, 1993) is joined to the N-terminal domain of TEAS, HVS, or CH9. Production of anti-malarial compounds is achieved using chimeric synthases having a C-terminal domain from artemisian synthase (El-Feraly et al., *J. Nat. Prod.* 52:196, 1989) and an N-terminal domain from TEAS, HVS, or CH9. Synthases capable of producing anti-tumor compounds are produced by joining the C-terminal domain of taxadiene synthase (Koepp et al., *J. Biol. Chem.* 270:8686, 1995) or helenalin synthase (Lee et al., *Science* 196: 533, 1977) with the N-terminal domain of TEAS, HVS, or CH9.

The invention is also useful for the production of chimeric synthases which are capable of generating insecticides. Such chimeric synthases are engineered by joining the C-terminal domain of cadenine synthase (Chen et al., *Arch. Biochem. Biophys.* 324: 255, 1995) to the N-terminal domain of TEAS, HVS, and CH9.

Finally, chimeric synthases are also useful for generating novel flavorings and perfumes. In one particular example, for the production of novel flavorings and aromas, a chimeric synthase is engineered by joining the C-terminal domain of limonene synthase (Colby et al., *J Biol. Chem.* 268: 23016, 1993) to the C-terminal domain of TEAS, HVS, or CH9.

All publications and patents mentioned in this specification are herein incorporated by reference to the same extent as if each individual publication or patent was specifically and individually indicated to be incorporated by reference.

Other Embodiments

From the foregoing description, one skilled in the art can easily ascertain the essential characteristics of this invention, and can make various changes and modifications of the invention to adapt it to various usages and conditions. Thus, other embodiments are also within the claims.

What is claimed is:

1. A chimeric isoprenoid synthase polypeptide, comprising a first sesquiterpene isoprenoid synthase polypeptide domain joined to a second, different, sesquiterpene isoprenoid synthase polypeptide domain such that the chimeric isoprenoid synthase polypeptide produces one or more isoprenoid products that are not produced in the absence of the second domain of the second synthase.

2. The chimeric isoprenoid synthase polypeptide of claim 1, wherein the chimeric synthase catalyzes the production of at least one isoprenoid sesquiterpene synthase reaction product that is not produced in the absence of the second isoprenoid synthase domain.

3. The chimeric isoprenoid synthase polypeptide of claim 1, wherein the isoprenoid reaction product(s) is/are cyclic.

4. The chimeric isoprenoid synthase polypeptide of claim 1, wherein the second domain also determines the ratio of isoprenoid reaction products.

5. The chimeric isoprenoid synthase polypeptide of claim 1, wherein the chimeric isoprenoid synthase polypeptide catalyzes production of at least two different isoprenoid reaction products.

6. The chimeric isoprenoid synthase polypeptide of claim 1, wherein:
the first isoprenoid synthase polypeptide is from a plant isoprenoid synthase; and the second, different, isoprenoid synthase polypeptide is from a second isoprenoid synthase.

7. The chimeric isoprenoid synthase polypeptide of claim 1, wherein the first isoprenoid synthase polypeptide is from tobacco and the second isoprenoid synthase polypeptide is from *Hyoscyamus*.

8. The chimeric isoprenoid synthase polypeptide of claim 1, wherein:
the isoprenoid synthase polypeptide catalyzes the production of an antifungal agent; or
the isoprenoid synthase polypeptide catalyzes the production of an antibacterial agent; or
the isoprenoid synthase polypeptide catalyzes the production of an antitumor agent; or the isoprenoid synthase polypeptide catalyzes the production of an antimalarial agent; or
the isoprenoid synthase polypeptide catalyzes the production of an insecticide.

9. The chimeric isoprenoid synthase polypeptide of claim 1, wherein the isoprenoid synthase polypeptide catalyzes the production of a compound suitable for the production of a flavoring or fragrance.

* * * * *

UNITED STATES PATENT AND TRADEMARK OFFICE
CERTIFICATE OF CORRECTION

PATENT NO. : 8,354,504 B2  Page 1 of 1
APPLICATION NO. : 12/927805
DATED : January 15, 2013
INVENTOR(S) : Chappell et al.

It is certified that error appears in the above-identified patent and that said Letters Patent is hereby corrected as shown below:

IN THE SPECIFICATION:

At column 4, line 67, replace ".sup.3H-FPP" with --$^{3}$H-FPP--; and

At column 6, lines 35-36, replace " 5'-d(GGGAGCTC<u>GAATTC</u>CATGGCCTC AGCAGCAGTTGCAAACTAT)-3' " with -- 5'-d(GGGAGCTC<u>GAATTC</u>CATGGCCTC AGCAGCAGTTGCAAACTAT)-3' --.

Signed and Sealed this
Twenty-fifth Day of June, 2013

Teresa Stanek Rea
*Acting Director of the United States Patent and Trademark Office*